(12) United States Patent
Rosenwasser et al.

(10) Patent No.: US 10,251,751 B2
(45) Date of Patent: Apr. 9, 2019

(54) CUSTOMIZED BENDABLE OSTEOCHONDRAL ALLOGRAFTS

(71) Applicant: THE TRUSTEES OF COLUMBIA UNIVERSITY IN THE CITY OF NEW YORK, New York, NY (US)

(72) Inventors: Melvin P. Rosenwasser, Palisades, NY (US); Gerard A. Ateshian, New York, NY (US); Clark T. Hung, New York, NY (US); Brian K. Jones, New York, NY (US)

(73) Assignee: The Trustees of Columbia University In The City of New York, New York, NY (US)

( * ) Notice: Subject to any disclaimer, the term of this patent is extended or adjusted under 35 U.S.C. 154(b) by 63 days.

(21) Appl. No.: 15/125,056

(22) PCT Filed: Mar. 11, 2015

(86) PCT No.: PCT/US2015/020033
§ 371 (c)(1),
(2) Date: Sep. 9, 2016

(87) PCT Pub. No.: WO2015/138652
PCT Pub. Date: Sep. 17, 2015

(65) Prior Publication Data
US 2017/0056181 A1    Mar. 2, 2017

Related U.S. Application Data

(60) Provisional application No. 61/951,630, filed on Mar. 12, 2014, provisional application No. 61/951,451, filed on Mar. 11, 2014.

(51) Int. Cl.
| | | |
|---|---|---|
| A61F 2/30 | (2006.01) | |
| A61F 2/28 | (2006.01) | |
| A61B 34/10 | (2016.01) | |

(52) U.S. Cl.
CPC .......... *A61F 2/30756* (2013.01); *A61B 34/10* (2016.02); *A61F 2/28* (2013.01); *A61B 2034/108* (2016.02); *A61F 2002/30538* (2013.01); *A61F 2002/30594* (2013.01)

(58) Field of Classification Search
CPC ....... A61F 2/30756; A61F 2/3603; A61F 2/28
See application file for complete search history.

(56) References Cited

U.S. PATENT DOCUMENTS

| | | |
|---|---|---|
| 8,483,863 B1 | 7/2013 | Knox |
| 9,168,140 B2 | 10/2015 | Shi et al. |
| 2003/0100947 A1 | 5/2003 | Nadler et al. |
| 2006/0178748 A1* | 8/2006 | Dinger, III ......... A61B 17/1615 623/18.11 |
| 2007/0233264 A1 | 10/2007 | Nycz et al. |
| 2007/0276506 A1 | 11/2007 | Troxel |
| 2008/0262616 A1 | 10/2008 | Mckay |
| 2008/0306490 A1 | 12/2008 | Lakin et al. |
| 2009/0204272 A1 | 8/2009 | Yuzawa |
| 2010/0256692 A1 | 10/2010 | Kang et al. |
| 2013/0096680 A1 | 4/2013 | Ribeiro et al. |
| 2014/0030309 A1 | 1/2014 | Yoo et al. |
| 2014/0271570 A1 | 9/2014 | Shi et al. |

* cited by examiner

*Primary Examiner* — Jason-Dennis Stewart
(74) *Attorney, Agent, or Firm* — Walter M. Egbert, III; Reed Smith LLP

(57) ABSTRACT

A customized allograft that is bendable and suitable for allo-grafting of an articular joint, including the thumb.

5 Claims, 24 Drawing Sheets

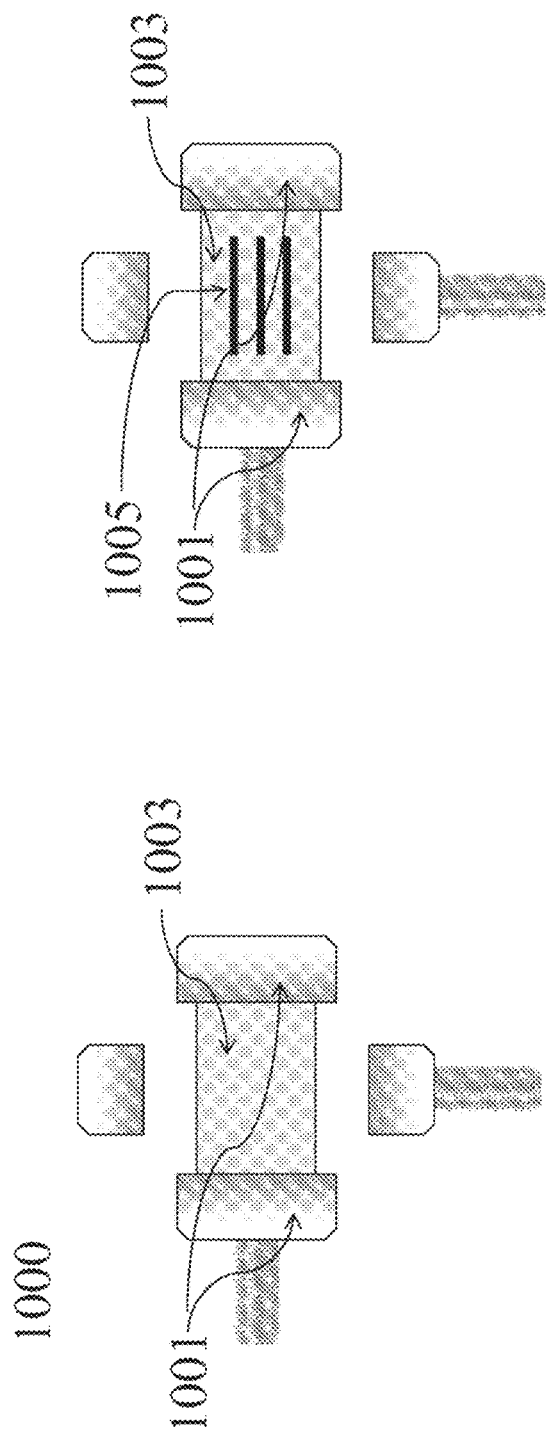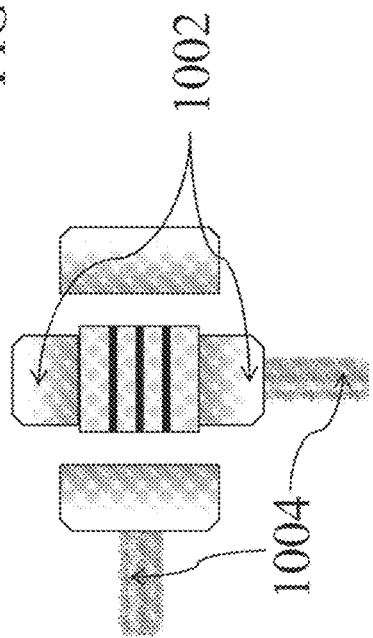
FIG. 10A
FIG. 10B
FIG. 10C

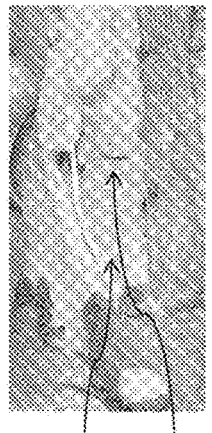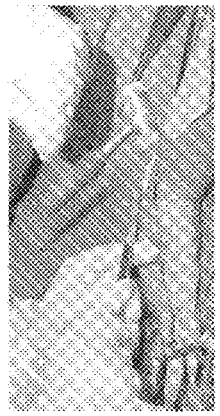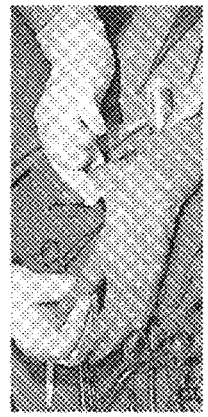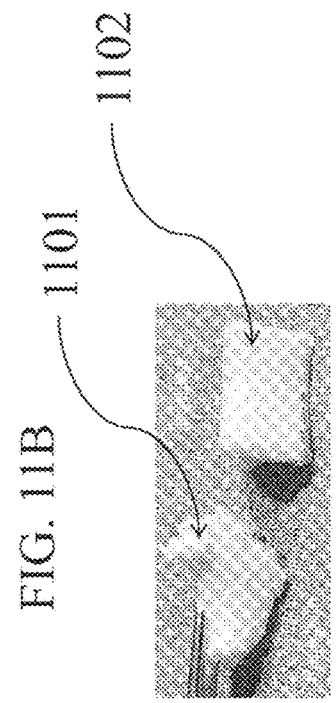

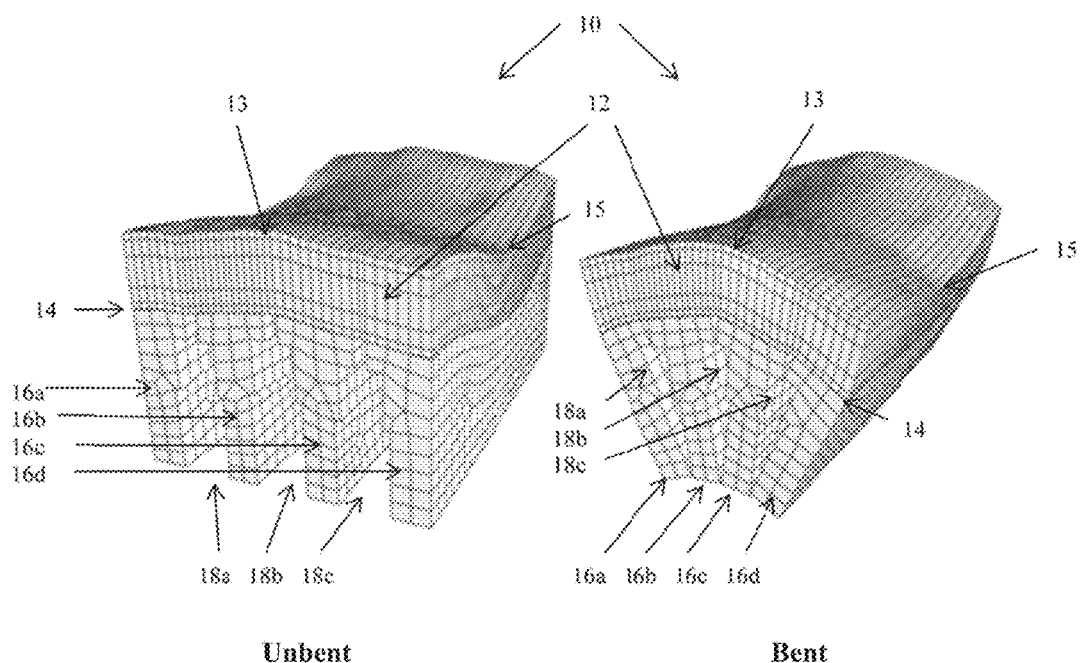
Unbent  
FIG. 16A
Bent  
FIG. 16B
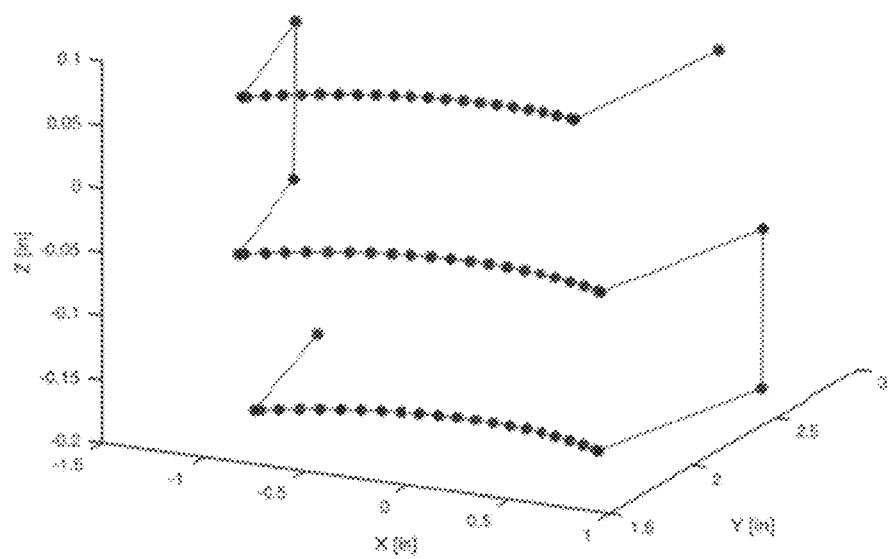
FIG. 17

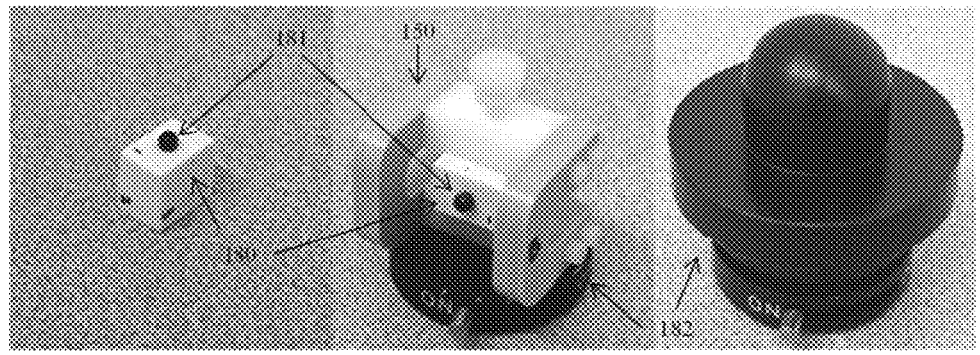
FIG. 18A  FIG. 18B  FIG. 18C
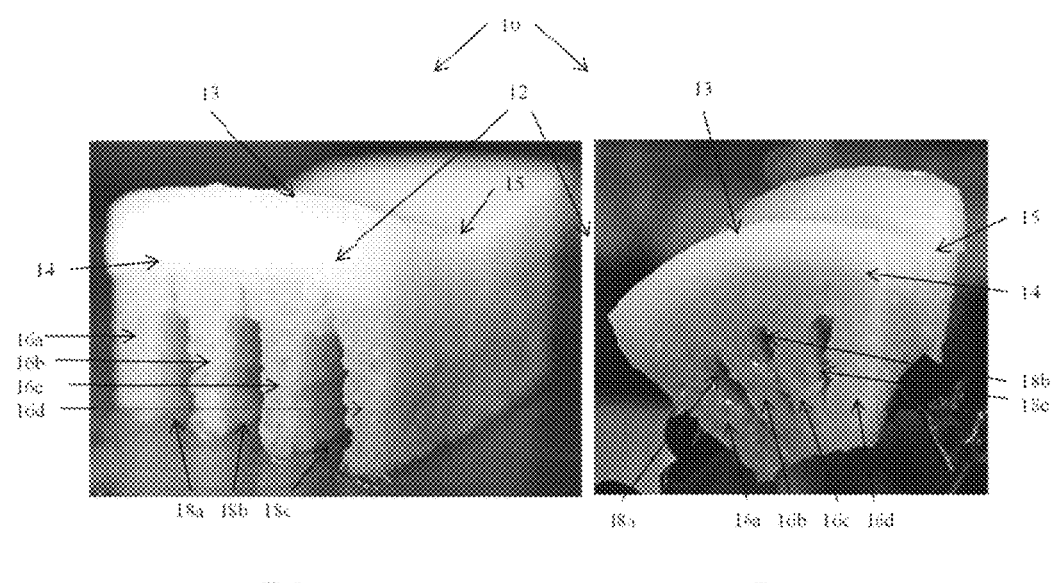
Unbent
FIG. 19A
Bent
FIG. 19A

CUSTOMIZED BENDABLE OSTEOCHONDRAL ALLOGRAFTS

CROSS REFERENCE TO RELATED APPLICATIONS

This application is a Continuation-in-Part application of International Application No. PCT/US2015/020033, filed Mar. 11, 2015, which claims the benefit of U.S. Provisional Application Nos. 61/951,451 and 61/951,630 filed on Mar. 11, 2014 and Mar. 12, 2014, the entirety of each of which is hereby incorporated by reference.

BACKGROUND OF THE DISCLOSED SUBJECT MATTER

Field

The disclosed subject matter relates to osteochondral allografts. Particularly, the presently disclosed subject matter relates to a customized osteochondral allograft that is specific to the host. The disclosed subject matter also relates to systems and methods for creating a customized osteochondral graft for a host site, a computer readable medium containing instructions executable to determine characteristics of a customized osteochondral graft, tools for creating and implanting a customized osteochondral graft, and a kit containing a customized osteochondral graft.

Background

Osteochondral allografting is a type of cartilage transplant procedure that can be used to treat individuals with cartilage injury or disease. However, there is a limited supply of osteochondral grafts, and it is very rare that an osteochondral graft will perfectly fit an individual's implant site. There is a need for durable, customizable osteochondral grafts.

SUMMARY

Articular cartilage is the smooth tissue that covers the ends of bones that meet at the joints. Healthy cartilage allows the bones to glide over each other with very little friction, and makes it easier to move. Articular cartilage can be damaged by injury or normal wear and tear. Because cartilage does not heal itself well, techniques have been developed to stimulate the growth of new cartilage. Restoring articular cartilage can relieve pain and allow better function. Most importantly, it can delay or prevent the onset of arthritis.

Osteochondral allografting is a type of cartilage transplant procedure used to treat individuals with cartilage injury or disease. The procedure involves transplanting a piece of articular cartilage and attached subchondral bone to a damaged section of the articular surface of a joint. Osteochondral allografting can provide viable or devitalized cartilage and supporting bone that will be sufficient to maintain joint function and thereby relieve pain and reduce further damage to the articulation.

Tendon interposition arthroplasty with ligament reconstruction is currently the preferred technique for the treatment of carpometacarpal (CMC) joint arthritis of the thumb by most surgeons. Ligament reconstruction with tendon interposition removes the pain-generating bone on bone surfaces and fills the void created by the trapeziectomy. The thumb, however, does not regain its total function. The thumb carpometacarpal (CMC) joint is the second most common site of osteoarthritis (OA) at 45 years of age, following the interphalangeal joints and preceding the tibiofemoral and hip joints. Thumb CMC joint osteoarthritis is a highly disabling condition since advanced osteoarthritis of the thumb implies fifty percent loss of hand function.

Finger joints tend not to be stored by tissue banks, because they are subject to substantial wear, and thus are unlikely to be suitable for transplant. Larger joints are generally stored in tissue banks, though the anatomy of various joints is not generally interchangeable. Joints are only retained for a limited time, and there is a limited supply. Each host site has a distinct geometry, and thus it is highly unlikely to find a perfectly fitting joint from which an osteochondral allografts can be taken.

There thus remains a need for durable osteochondral grafts customized to an implant site, including the thumb joint.

The ideal arthroplasty for diarthrodial joints such as the thumb, shoulder, knee and hip is one that will substantially reproduce the correct anatomy of its articular surfaces to maintain its natural motions, reproduce the joint height to maintain normal strength, and provide a healthy and relatively thick articular layer that can reproduce the compliance and congruence of the natural joint under physiologic loading. To achieve this goal, osteochondral allografts (either live or frozen) harvested from a variety of donor joints are provided that may be bent to match the natural surface curvatures of the host transplantation site.

In one aspect, a customized allograft is provided. The customized allograft comprises an uninterrupted cartilaginous layer having a first surface disposed on a bone portion. The bone portion has one or more grooves cut across the width of the bone portion that allows for bending and conformation of the allograft to match a host site.

In another aspect, methods are provided to map grooves in the subchondral bone to allow bending of these allografts to alter the curvature and substantially match it to that of the natural articular layers at the host site, while maintaining a level of cartilage strains that preclude mechanical failure (in live and frozen allografts) and excessive cell death (in live allografts).

In one embodiment, the method for bending osteochondral allografts to match the desired curvatures includes one or more of the following steps: (1) characterizing the surface curvature of the host site or that of the contralateral joint; (2) finding the closest match in curvature from a database of curvatures acquired from donor osteochondral allografts, not necessarily from the same anatomic joint as the host; (3) based on the degree of curvature matching between host and donor, determine the amount of bending required and identify one or more of the number, width, and orientation of grooves carved in the bony side of the osteochondral allograft suitable to reproduce the desired bending; (4) performing analyses of the state of strain produced in the allograft cartilage layer as a result of the bending; (5) optimizing the groove pattern and geometry to ensure that the largest tensile strain does not exceed about 16% and the largest compressive strain does not exceed about 50%, to maintain mechanical integrity and cell viability; (6) optionally, grooves may be chamfered (mortar groove) or dovetailed to facilitate the bending to increase or decrease curvature while removing as little bone as necessary; and (7) optionally, the peripheral boundaries of osteochondral allografts may be contoured using a side-cutting burr or other tool to match the contour of the host recipient site.

This method increases the applicability and effectiveness of osteochondral allograft transplantation by matching the natural anatomy of the host site even when the donor site is from a different anatomical location (e.g., from knee to thumb). The method is effective with surfaces that have convex curvatures, concave curvatures, or a mix of convex and concave curvatures (saddle-shaped). Much less waste is produced from donor joints that could not be previously matched to host sites within the short viability window of live osteochondral allografts, since curvature matching can be achieved according to the subject matter of the present disclosure.

In another aspect, a system is provided to preparing a customized osteochondral graft, the system comprises a database comprising information related to a plurality of allografts; a processor configured to: receive a description of a host site; select a first allograft from the database such that the first allograft is suitable for transplantation to the host site; determine an amount of bending suitable to conform the first allograft to the host site; and determine a groove pattern for the first allograft based on the determined amount of bending, wherein the groove pattern if cut into the first allograft provides a customized allograft conforming to the host site.

In another aspect, a device for customizing an osteochondral allograft is provided. The device comprises a clamp adapted to retain a graft along a first axis and a second axis of the graft, a cutter adapted to cut a groove in the graft, and a sensor adapted to determine the depth of the groove during cutting.

In one embodiment, the clamp comprises a first pair of substantially parallel surfaces, each of the first pair having a center point, the center points of each of the first pair defining a first axis, and a second pair of substantially parallel surfaces, each of the second pair having a center point, the center points of each of the second pair defining a second axis. The second pair of substantially parallel surfaces is arrayed substantially perpendicularly to the first pair, such that the first axis and the second axis cross at a point substantially between the first and second pairs.

In another embodiment, the sensor comprises a light emitter positioned to emit light into the groove and a light detector positioned to detect light passing through the graft from the light emitter.

In another aspect, a method for preparing an osteochondral allograft is provided, comprising selecting a donor graft and retaining the donor graft between opposed surfaces of a first clamp. At least one groove is cut in the donor graft and the donor graft is retained between opposed surfaces of a second clamp. The first clamp is released and the donor graft is cut to form at least one edge, the edge being substantially perpendicular to the groove. In some embodiments, the depth of the groove is measured during cutting. In some embodiments, the depth is measured by measuring the light transmissivity of the graft.

It is to be understood that both the foregoing general description and the following detailed description are exemplary and are intended to provide further explanation of the disclosed subject matter claimed. The accompanying drawings, which are incorporated in and constitute part of this specification, are included to illustrate and provide a further understanding of the method and system of the disclosed subject matter. Together with the description, the drawings serve to explain the principles of the disclosed subject matter.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part. Similar reference numerals (differentiated by the leading numeral) may be provided among the various views and Figures presented herein to denote functionally corresponding, but not necessarily identical structures.

FIGS. 10A-10C depict the use of a motorized two-axis clamp to prepare an osteochondral allograft for implantation.

FIGS. 11A-I depict an exemplary surgery using the distal femoral trochlea as an allograft source for implantation into a cadaver hand according to an embodiment of the present disclosure.

FIGS. 16A-B shows finite element analysis plots of an allograft in unbent and bent configurations.

FIG. 17 shows a plot of a G-code tool path for cutting grooves in an allograft.

FIGS. 18A-C show photographic views of reference block and holding devices to calibrate the laser measuring and CNC machine systems.

FIGS. 19A and 19B show photographic images of a custom-machined allograft according to this disclosure in unbent and bent configurations.

DETAILED DESCRIPTION OF EXEMPLARY EMBODIMENTS

The presently disclosed subject matter relates to a customized osteochondral allograft that is specific to the host. The disclosed subject matter also relates to systems and methods for creating a customized osteochondral graft for a host site, a computer readable medium containing instructions executable to determine characteristics of a customized osteochondral graft, tools for creating and implanting a customized osteochondral graft, and a kit containing a customized osteochondral graft.

Reference will now be made in detail to exemplary embodiments of the disclosed subject matter, an example of which is illustrated in the accompanying drawings. Methods and corresponding steps of the disclosed subject matter will be described in conjunction with the detailed description of the system.

Figure 1A:
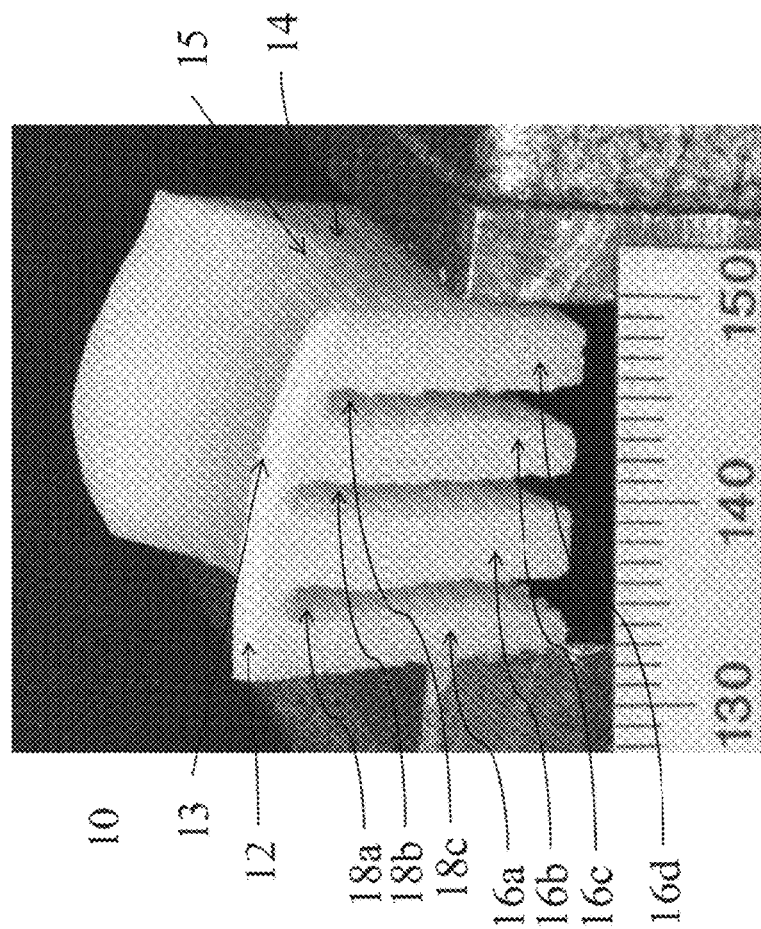
FIG. 1A-B depict a grooved femoral trochlear osteochondral allograft according to an embodiment of the present disclosure.
Figure 1B:
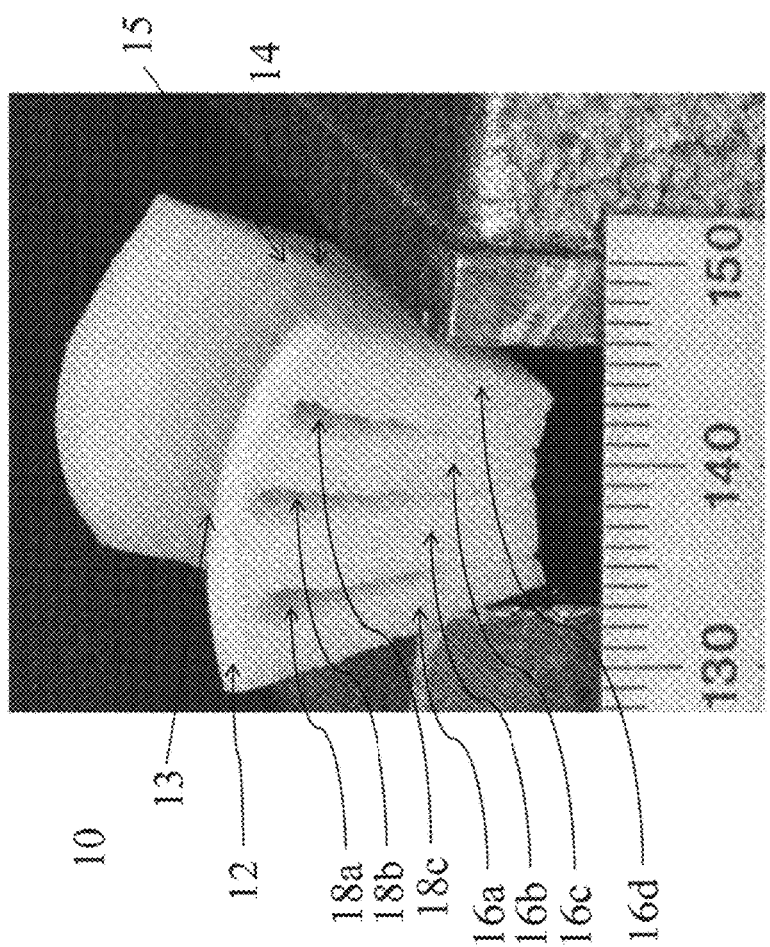
Figures 8A, 8B, 8C:
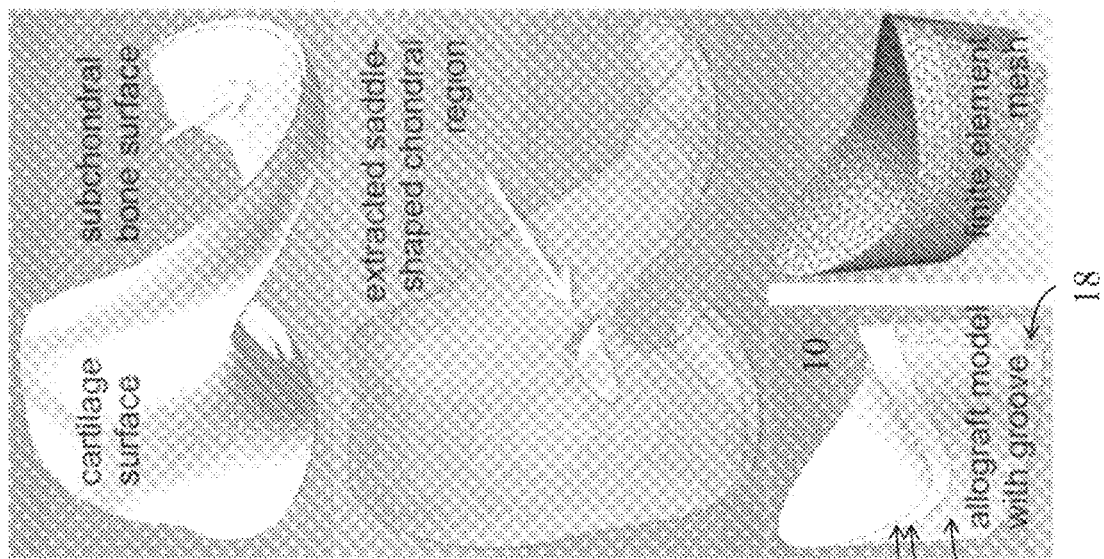
FIG. 8A depicts B-splines of cartilage and bone surfaces of human distal femur.
FIG. 8B depicts a chondral region extracted from location matching trapezium curvatures most closely (FIG. 4).
FIG. 8C depicts an osteochondral allograft model created using solid modeling software, meshed for finite element analysis.

In one aspect of the disclosed subject matter, a whole block cartilage allograft with an intact surface avoids the biologic problem of graft adherence to the host cartilage when used as a partial filler of focal defects, as is now used clinically. There are no generally accepted and reliably successful small joint implants for hand arthritis and as stated there is a high incidence which is clinically significant. Thus, in accordance with one aspect of the disclosed subject matter, customized osteochondral grafts as shown in FIGS. 1A, 1B, and 8C is provided. The customized osteochondral graft 10 has an uninterrupted cartilaginous layer 12 having a first surface 14 disposed on a bone portion 16. The bone portion 16 having one or more grooves 18. The customized graft is bendable into a shape that conforms to a host site. In one embodiment, as depicted in FIG. 8C, the graft can have one groove. In other embodiments, as shown in FIGS. 1A and 1B, the graft 10 has a plurality of bone portions 16a, 16b, 16c, 16d, created by a plurality of grooves 18a, 18b, 18c spaced into the bone section 16. The uninterrupted cartilaginous layer preferably has a saddle shape. In some embodiments, the uninterrupted cartilaginous layer is saddle-shaped. The ideal arthroplasty for the thumb CMC joint reproduces the saddle-shaped anatomy of its articular surfaces to maintain its natural motions, reproduce the joint height to maintain normal strength, and provide a healthy and relatively thick articular layer that can reproduce the compliance and congruence of the natural joint under various pinch and grasp forces.

To achieve this goal, osteochondral allografts harvested from saddle-shaped regions of articular layers from the trochleas of the distal femur, distal humerus, proximal ulna or the talus, can be used to replace the distal half of the trapezium. Grooves are created in the subchondral bone to allow gentle bending of the allografts for increasing their curvature and matching it to that of the natural CMC articular layers. This allows the normal anatomical motions of this joint to be reproduced. Such allografts provide all the desired benefits of the ideal arthroplasty. The following steps achieve this goal.

Saddle-shaped osteochondral allografts may be taken from various human diarthrodial joints having trochlear surfaces (knee, elbow, ankle) for transplantation. These may be selected by finding regions of articular surfaces whose curvatures and surface area match most closely those of the host site (e.g., the trapezial surface of the thumb CMC joint) and whose cartilage thickness at least matches the combined thicknesses of the region surrounding the host site (e.g., trapezium and metacarpal articular layers). In some embodiments, cartilage thickness is selected to be greater than the natural thickness of the host site cartilage, to compensate for any graft attrition and to allow for better fixation in the subcortical bone mantle. Fresh frozen cadaver joints may be acquired from tissue banks and their articular layer geometry characterized using a fast 3D laser scanner. In other embodiments of present disclosure, alternative contact and non-contact 3D scanning approaches are used. These include coordinate measuring machines (CMM); time-of-flight 3D laser scanners; triangulation based 3D laser scanners; conoscopic holography; structured-light 3D scanners; modulated light 3D scanners; computed tomography (CT); magnetic resonance imaging (MRI); stereoscopic systems; photometric systems; silhouette techniques; photogrammetric methods; and alternative light, ultrasound or x-ray based scanners. Surface curvature and cartilage thickness may be quantitatively assessed.

Once measurements are taken of a joint by a 3D scanning method, the shape data is stored in a computer readable medium for later retrieval. In some embodiments, the raw data is converted into a triangulated mesh prior to storage. In some embodiments, a triangulated mesh is converted into a computer-aided design (CAD) model. For example, the model may include nonuniform rational B-spline surfaces. In alternative embodiment, a discrete 3D volumetric representation is generated from the raw data. In some embodiments, the joint geometry data is stored in a database, while in other embodiment the joint geometry is stored in flat files in a filesystem.

In some embodiments, the host site is characterized using one of the methods described above with respect to characterization of a donor joint. In such embodiments, the host site is compared with the stored donor joints. The comparison may be performed manually, for example by displaying 3D models of the various donor joints and the host site for human comparison. The comparison may also be performed automatically, for example using various surface matching algorithms to compare the surface contour and curvature of the host site with each of the donor joints in a database. In some embodiments, the comparison is performed by least squares 3D surface matching. In other embodiments, an approximation based similarity search is performed. In some embodiments, a closest match is determined from the database of donor joints without deformation of the donor joint surface. However, in other embodiments, deformable surface matching algorithms are used to find a donor joint that may be deformed to provide a close match to the host site using according to the methods described herein.

Based upon the surface characterization of the donor joint, a groove pattern is computed to be carved in the bony side of the osteochondral allografts. The pattern is computed to have the minimum width and number of grooves suitable to bend the allograft to the desired curvature to match the host site, without causing measurable damage to the articular layer and without compromising the implanted allograft's structural integrity under physiological joint loads. In some embodiments, grooves are carved along the radio-ulnar and dorsal-volar directions. In some embodiments, finite element modeling is used to determine the number and width of grooves that will produce the desired surface curvature upon bending, while maintaining cartilage strains at or below tolerable levels. In some embodiments, a mechanical loading of several suitably grooved and bent osteochondral allografts may be transplanted in cadaver hands to assess their mechanical integrity under physiological load magnitudes and to narrow down the best source of allografts for a given host site.

In some embodiments, a search space is defined comprising the various donor joints and groove patterns. A closest matching combination of donor joint and groove pattern resulting in a minimum of strain is determined using mathematical optimization methods. However, various alternative optimization algorithms and approaches may be used including dynamic programming techniques, steepest descent methods, conjugate gradient methods, simulated annealing, and genetic algorithms.

The distal femoral trochlea provides a valid source of osteochondral allografts with sufficiently thick cartilage (>2 mm), a concave curvature in the medial-lateral direction that matches the trapezial concavity in the radial-ulnar direction, requiring only bending to increase the convexity in the anterior-posterior direction to match that of the trapezium in the dorsal-volar direction. Other trochlear surfaces require less bending. Live cartilage can sustain compressive strains up to 50% with minimal loss of cell viability. Thus, bending of live osteochondral allografts does not cause significant cell death. Finally, cutting grooves and bending osteochondral allografts may be performed according to embodiments of the present disclosure with no visible mechanical damage. Additionally, grooves may be created in such a manner that graft viability and sterility is maintained. In some embodiments, software algorithms and sensors are used to determine proper groove depth.

In some embodiments the cutting tools are software-driven to cut grooves in the bony side of osteochondral allografts based on the groove pattern identified according to the methods outlined above. In some embodiments, the requisite groove depth allowing for safe bending of the allograft is computed by a computer. In some embodiments, sensors detect the depth of the grooves in the bone and their closeness to the articular layer, adjusting the depth of the cut using a feedback control algorithm.

Referring now to FIG. 1, an exemplary osteochondral graft 10 according to an embodiment of the present disclosure is depicted. In FIG. 1, cartilaginous layer 12 is saddle shaped. Bone layer 16 is cut by a plurality of grooves 18, which do not penetrate cartilaginous layer 12. In FIG. 1A, the graft is unbent. In FIG. 1B, the graft is bent, narrowing grooves 18 and changing the saddle shape of cartilaginous layer 12 to better match a host site. Allograft 10 can bend significantly to increase its curvature, without damage. Comparison of the unbent graft in FIG. 1A with the bent graft in FIG. 1B shows increased curvature of the cartilage layer 12 in the direction perpendicular to the orientation 13 of the grooves 18, while the curvature of the graft in the direction parallel to the orientation 15 of the grooves 18 remains significantly unchanged.

Figure 2:
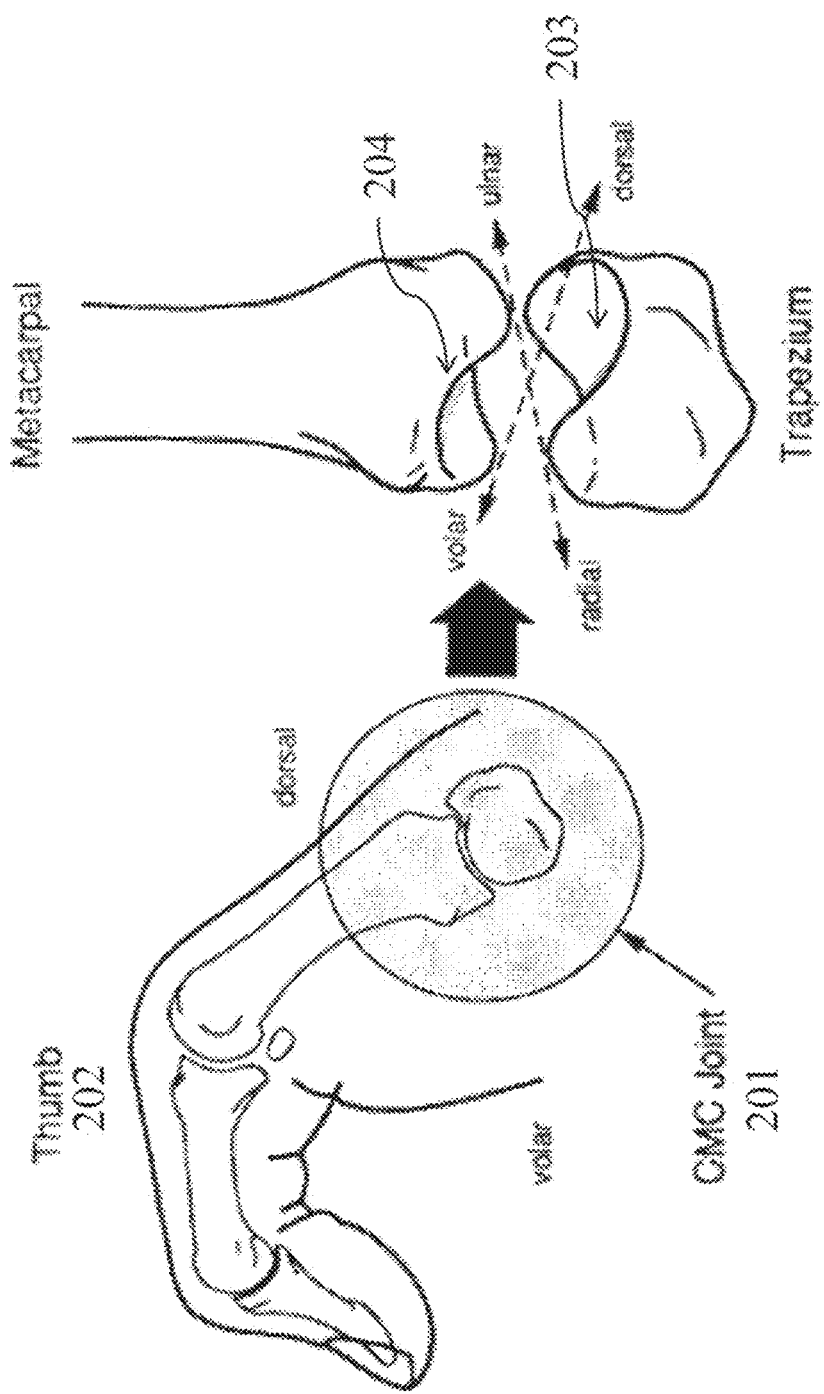
FIG. 2 depicts the characteristic saddle shape of the articular surfaces of the carpometacarpal (CMC) joint of the thumb.

Referring now to FIG. 2, the thumb CMC joint 201 is located at the base of the thumb 202 and its articular surfaces 203, 204 are often described as saddle-shaped (convex along one direction and concave along the corresponding perpendicular direction). This anatomy provides large ranges of motion in flexion-extension and abduction-adduction along the principal curvature directions of the saddle surfaces, but limits the range of pronation-supination in conjunction with capsular ligamentous constraints. This joint is the second most common site of osteoarthritis (OA) at 45 years of age, following the interphalangeal joints and preceding the tibiofemoral and hip joints. Various epidemiological studies have indicated that radiographic changes in this joint are present in more than one out of every six women older than 45 years of age, and in 5% of all men. In the age group 55-64, radiographic evidence of moderate and severe OA have been observed in 16% of women and 6.4% of men. While thumb CMC joint OA ranks second in frequency behind the interphalangeal joints of the fingers, it is a more disabling and functionally significant condition since advanced OA of the thumb implies fifty percent loss of hand function.

Artificial joint replacement in the fingers has not enjoyed the same successes as in the hip, knee or shoulder joints, primarily due to the absence of a successful artificial joint design that can reproduce the normal anatomical range of motion of this saddle-shaped joint. Artificial replacements for the thumb CMC joint include the Swanson trapezial implant, the Swanson condylar implant, the De la Caffiniere prosthesis, the Braun design, the Kessler design, the Mayo clinic prosthesis, the Helal spacer, the Eaton trapezial implant, and the Niebauer "tie-in" design. Of these various designs, the Swanson trapezial implant initially gained significant popularity, until its usage was discontinued due to instability of the prosthesis and particle-induced synovitis. Other designs have generally been beset by similar complications.

Treatment modalities for thumb CMC OA are therefore limited. The most common treatment for advanced CMC OA today is tendon interposition arthroplasty with ligament reconstruction, which involves total resection of the trapezium. Though this procedure has been successful at alleviating pain and returning significant range of motion, it produces significant loss of pinch strength due to the reduced height of the joint. Other than tendon interposition, allograft arthroplasties for the CMC joint have been limited, with some reports using costochondral allografts and acellular dermal allografts. The use of trapezial allografts has not been reported, because such allografts would likely have little cartilage left to provide the necessary function required for this joint.

Osteochondral allograft transplantation has demonstrated favorable outcomes, particularly in the knee, but also in the ankle and preliminarily in the shoulder. All allograft transplantations require trimming operations that may partially compromise their mechanical integrity and, in the case of live tissue allografts, their cell viability. The safety of osteochondral allografts according to the present disclosure are comparable to alternative allograft transplantation procedures. Although various examples herein refer to the finger joints, the subject matter of the present disclosure is applicable to many other joints, significantly expanding the use of allografts.

Figure 3A:
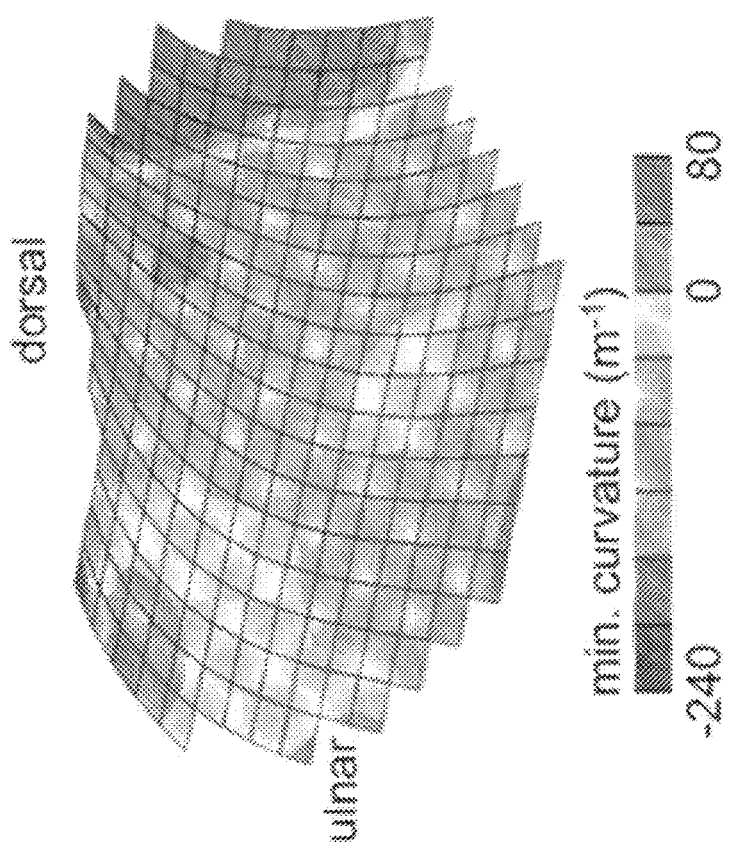
FIGS. 3A-B depict exemplary minimum and maximum curvature maps of the human trapezium articular surface.
Figure 3B:
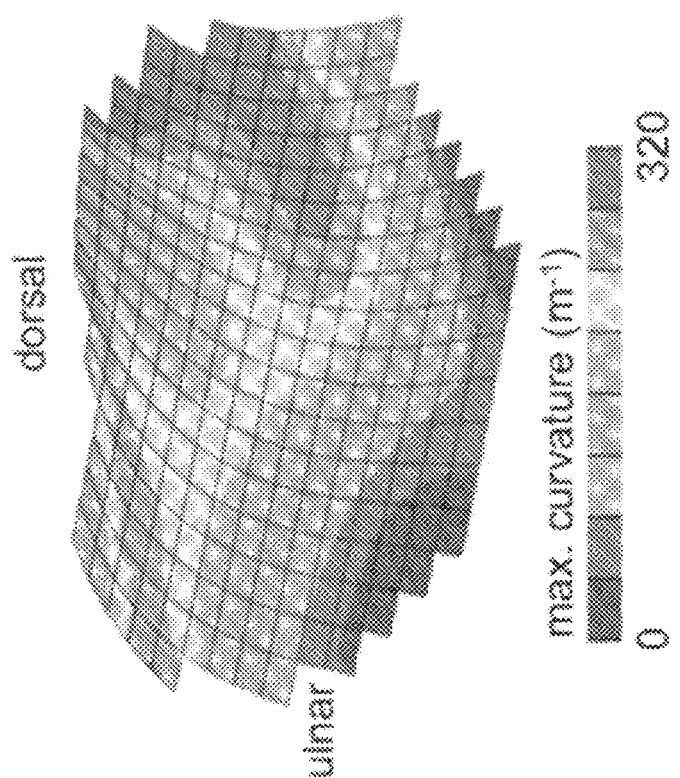

Referring now to FIG. 3, exemplary minimum (FIG. 3A) and maximum (FIG. 3B) curvature maps of the human trapezium articular surface are provided. In some embodiments of the present disclosure, stereophotogrammetry (using photography from two different directions) is used for reconstructing the three-dimensional (3D) topography of the human knee joint and the thickness of its articular layers. In some embodiments, stereophotogrammetry is similarly used to reconstruct the 3D topography of the human thumb CMC joint articular surfaces and map the surface curvatures of these articular layers (FIG. 3). In the exemplary joint of FIG. 3, the trapezium surface area is measured at $1.27 \pm 0.35$ cm$^2$. The minimum curvature (the concavity along the radio-ulnar direction) averages $-71 \pm 24$ m$^{-1}$ (equivalent to a radius of curvature of 14 mm). The maximum curvature (the convexity along the dorsal-volar direction) averages 161±48 m$^{-1}$ (radius of curvature of 6.2 mm). In some embodiments, these ranges serve as the targeted curvatures to be achieved by bending osteochondral allografts.

Stereophotogrammetric study of 46 human thumb CMC joints also reports the thickness of the articular layers, with values of 0.89±0.16 mm reported for the trapezium and 0.89±0.15 mm for the metacarpal of the least degenerated joints (n=8). From these prior measurements, it may be concluded that the combined thickness of the trapezium and metacarpal articular layers averages approximately 1.8±0.2 mm. In some embodiments, this thickness range serves as the targeted minimum thickness desired for osteochondral allografts to be used in the thumb CMC joint.

Figure 4A:
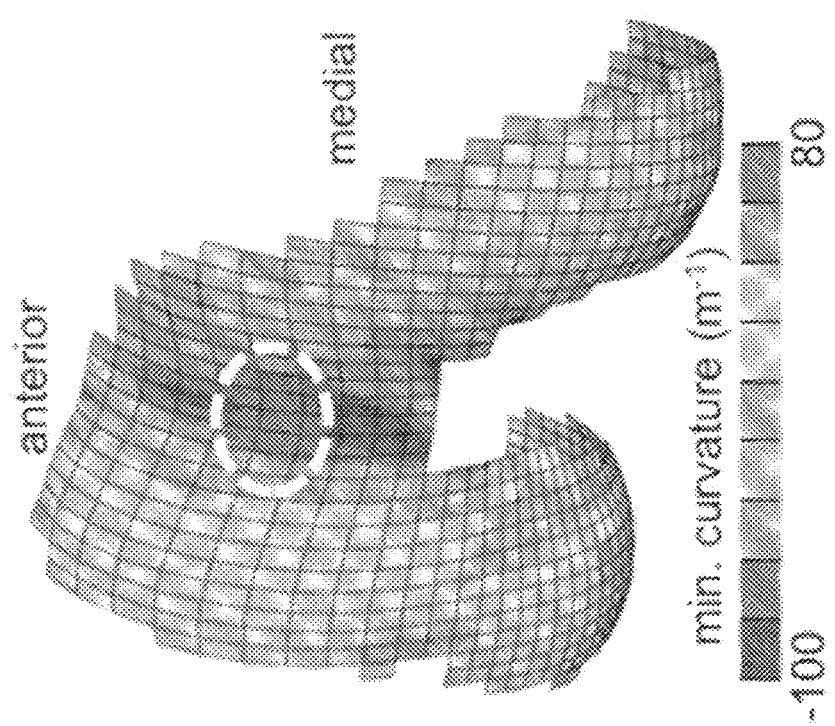
FIGS. 4A-B depict exemplary minimum and maximum curvature contour maps of the human distal femoral articular surface.
Figure 4B:
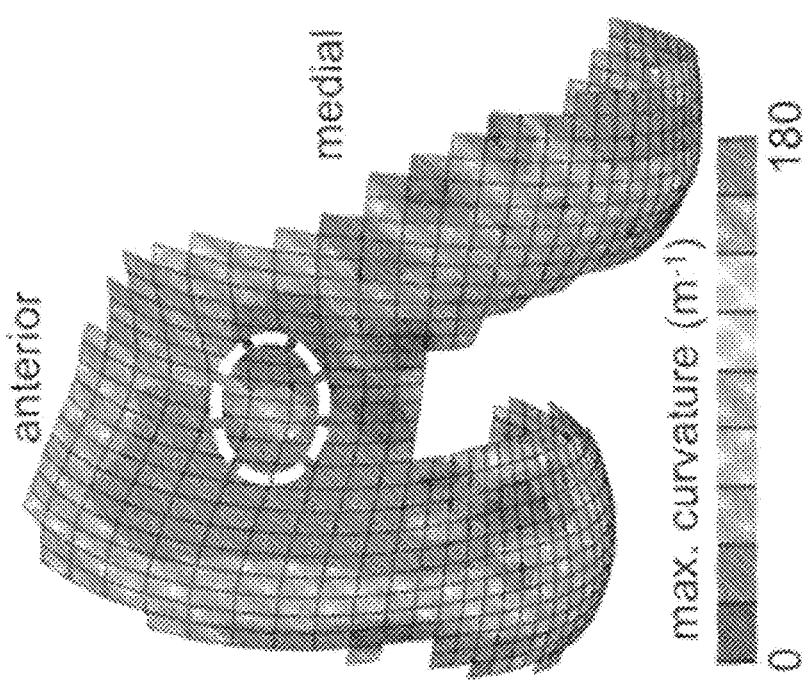

Referring now to FIG. 4, the curvature magnitudes of the human patellofemoral joint vary along the length of the groove; curvature maps of the average distal femoral topography show that locations exist where the minimum curvature is approximately −70 m$^{-1}$ (FIG. 4A), consistent with that of the trapezial articular surface, whereas the maximum curvature at that location is approximately 50 m$^{-1}$ (FIG. 4B). Thus, bending of an osteochondral allograft harvested from the human distal femoral trochlea may increase the maximum curvature to match that of the trapezium. In this figure, the dashed curve indicates region matching minimum curvature of trapezium.

Figure 5:
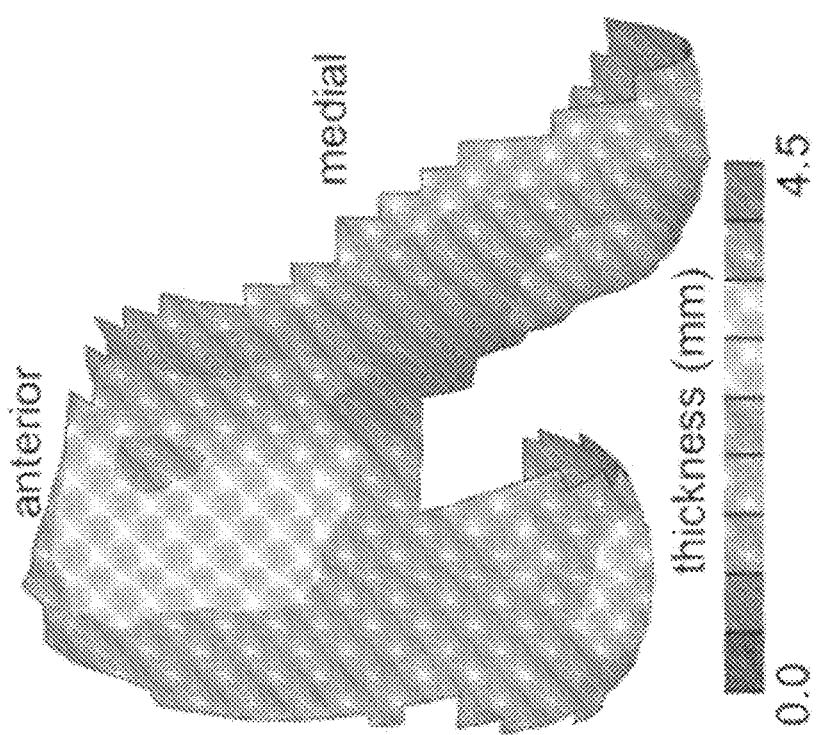
FIG. 5 depicts an average thickness map of human distal femoral cartilage.

Referring now to FIG. 5, in some embodiments, 3D measurements of articular layer surface topography and cartilage thickness are acquired from magnetic resonance imaging (MRI). Using such methods, the average cartilage thickness of the distal femoral trochlea may be measured to range from 2.1±0.4 near the intercondylar notch, to 4.3±1.1 mm at the anterior trochlea (FIG. 5). Thus, it is possible to match the minimum targeted thickness for trapezium osteochondral allografts harvested from the distal femoral trochlea.

Bending an osteochondral allograft subjects the articular layer to large deformations and finite strains. Thus, bending must remain within the range of strains for which bending does not cause cartilage failure. Cartilage does not fail under compression, even for compressive strains up to 50%. Under tension, cartilage does not fail up to 16% strain. Normal strain patterns in the distal femoral trochlea range from −11%±5% in compression to 12%±2% in tension. Thus, cartilage strains up to 50% in compression and 16% in tension are mechanically safe ranges for human cartilage. This criterion is used according to various embodiments of the present disclosure when assessing the safe amount of osteochondral bending that preserves the mechanical integrity of the cartilage layer. To predict the amount of strain caused by bending of osteochondral allografts, the finite element method is used to model cartilage as a biphasic material exhibiting tension-compression nonlinearity, using representative material properties from experimental studies. In some embodiments, the open-source finite element code FEBio (www.febio.org) is used.

Figure 6:
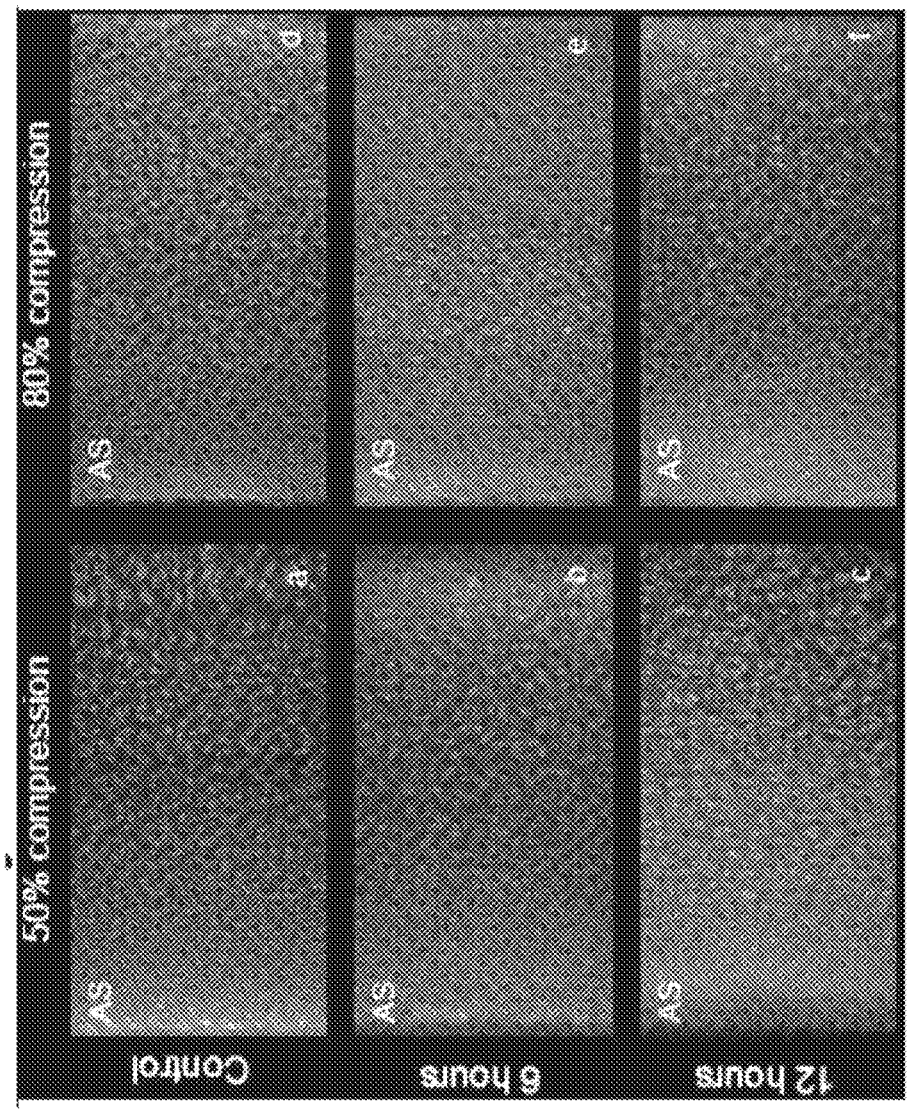
FIG. 6 depicts chondrocyte viability in immature bovine explants subjected to 0%, 50% and 80% compressive strain for up to 12 h.

The viability of chondrocytes has been studied in live immature bovine cartilage explants subjected to compressive strains of 0%, 50% and 80%, for up to 12 h (FIG. 6). Results have demonstrated that at 50% compressive strain, cell viability is compromised only in the topmost superficial zone of the explants, whereas cells in the middle and deep zone remained viable. However, at 80% compression cells throughout the thickness of the articular layer become compromised. Thus, cell viability in the middle and deep zones can be maintained even when bending of osteochondral constructs produces 50% compressive strains at those locations.

Immature bovine chondral and osteochondral explants can maintain cell viability and collagen content, and slightly increase their proteoglycan content and compressive modulus, when cultured in a serumfree chondrogenic medium for up to six weeks. In contrast, explants cultured in media containing 20% fetal bovine serum exhibit significant loss of biochemical composition and mechanical properties. Mature bovine and canine osteochondral explants do not require dexamethasone when cultured in serumfree chondrogenic media in order to maintain their cell viability, biochemical composition and mechanical properties for up to 4 weeks in culture.

Using a trapezium allograft is often not suitable for treating thumb CMC joint OA because most donor allografts will exhibit some amount of degeneration, since OA manifests itself at an early age in this joint. Furthermore, even in the case of relatively healthy allografts, the trapezium articular layer thickness may not suffice to compensate for the loss of cartilage on the metacarpal. Therefore, an allograft with a suitably thick articular layer is needed. Bending of an osteochondral allograft according to the present disclosure reproduces the proper anatomical motions of the thumb joint. In contrast, tendon interposition arthroplasty does not attempt to reproduce the anatomical shape of the trapezium, since the compliance of the tendon adapts to the shape of the apposing metacarpal surface. That same compliance is responsible for weakening the thumb's pinch strength, since the use of an exclusively soft tissue allograft cannot maintain joint height. Costochondral allografts transplanted using a hemi-trapeziectomy likewise do not reproduce the saddle-shaped anatomy needed for pinch and grasp functions. An osteochondral allograft as disclosed herein provides a stiff bony substrate that maintains the desired height, while the articular layer guides the motion of the joint.

According to some embodiments of the present disclosure, a comprehensive database of potential donor joints is compiled by identifying as many suitable sources of osteochondral allografts as are available, with the aim of matching the principal (maximum and minimum) curvatures of the trapezium articular surface and the combined cartilage thickness of the trapezium and metacarpal as closely as possible. The closer the match in curvature, the lesser the bending required, and thus the lesser the risk of causing mechanical damage or loss of cell viability in the allograft cartilage layer. Therefore, articular surfaces that are naturally saddle-shaped (convex along one direction and concave in the perpendicular direction) serve as the best allograft source for this particular joint. As discussed above with regard to FIGS. 4-5, the distal femoral trochlea is suitable as a donor site. Other sources may include the talar trochlea, the distal humeral trochlea, and the proximal ulnar trochlea (semilunar notch). Sources exhibiting lesser usage than the knee are preferred, as are those that require less bending to reproduce the curvature of the trapezium.

In some embodiments, a computational modeling approach is used to perform a parametric analysis for the number and width of grooves necessary to maintain cartilage strains below the tolerable range. The fewer the grooves, the wider they need to be to allow a given amount of bending. Having all the bending localized in the cartilage layer above a single groove causes greater strains than in the case of multiple grooves that are each subjected to less bending. However increasing the number of grooves decreases the bone stock available in the osteochondral allograft and increases the number of allograft trimming steps. Therefore, a computational approach is used to efficiently balance these competing requirements and identify optimal groove number and geometry. Experimental measurements of thumb joints may be used to test the mechanical integrity of the allografts identified, which will be bent using the optimal groove numbers and geometries identified according to the computational component. These experimental measurements help to verify the maximum compressive load that may be sustained by grooved and bent allografts, in comparison to trapezium autografts serving as controls. The source of allograft that sustains the greatest amount of load is deemed the best candidates for clinical usage.

While some amount of cell loss occurs in living allografts from these manipulations, most cells remain alive.

In some embodiments, fresh-frozen elbow and ankle joints are obtained from a tissue bank for the purpose of characterizing the articular layer geometry (surface topography and curvature, and cartilage thickness) of the humeral trochlea, the ulnar trochlea, and the talar trochlea. A variety of male and female specimens may be used for each type of joint, to span a range of sizes representative of these joints for each gender. In some embodiments, prior characterizations of articular layer geometry may be used instead of collecting new geometric data. In general, candidate donor joints are under the age of 65 and do not exhibit excessive degeneration.

Referring now to FIG. 7, in some embodiments, joint characterization is performed using a 3D scanner. Each fresh-frozen joint is sharply dissected to expose the corresponding trochlear articular layer. The cartilage is kept moist using gauze soaked with physiological buffered saline (PBS). The articular layer and underlying bone are separated from the rest of the bone using a sagittal saw, and mounted on a backing plate with cyanoacrylate glue (FIG. 7A). The articular surface is scanned with a 3D laser scanner (FIG. 7B), along with fiducial markers located on the backing plate. This scanning process, which requires less than one minute, produces 3D coordinates of surface points at a density of 16 points/mm and a rated accuracy of 125 µm. Subsequently, the articular layer is dissolved in a 5.25% solution of sodium hypochlorite (household bleach), a process that requires three to six hours. The underlying subchondral plate is laser scanned, along with the fiducial markers on the backing plate. The fiducial marker data is used to register the 3D coordinates of the articular and subchondral bones surfaces into a common coordinate system (FIG. 7C). Maps of the cartilage thickness (FIG. 5) are generated. In addition to the topographic measurements of the humeral, ulnar and talar trochleas described herein, existing databases of femoral trochlea measurements acquired from stereophotogrammetry and MRI are used.

Figure 7A:
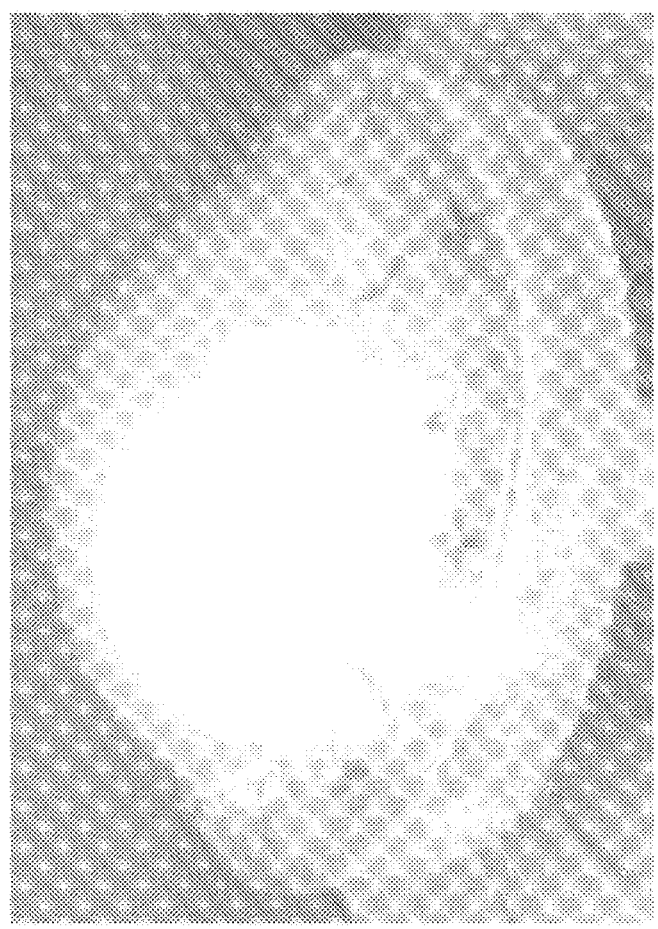
FIG. 7A depicts an immature bovine humeral head articular layer mounted on a backing plate.
Figure 7B:
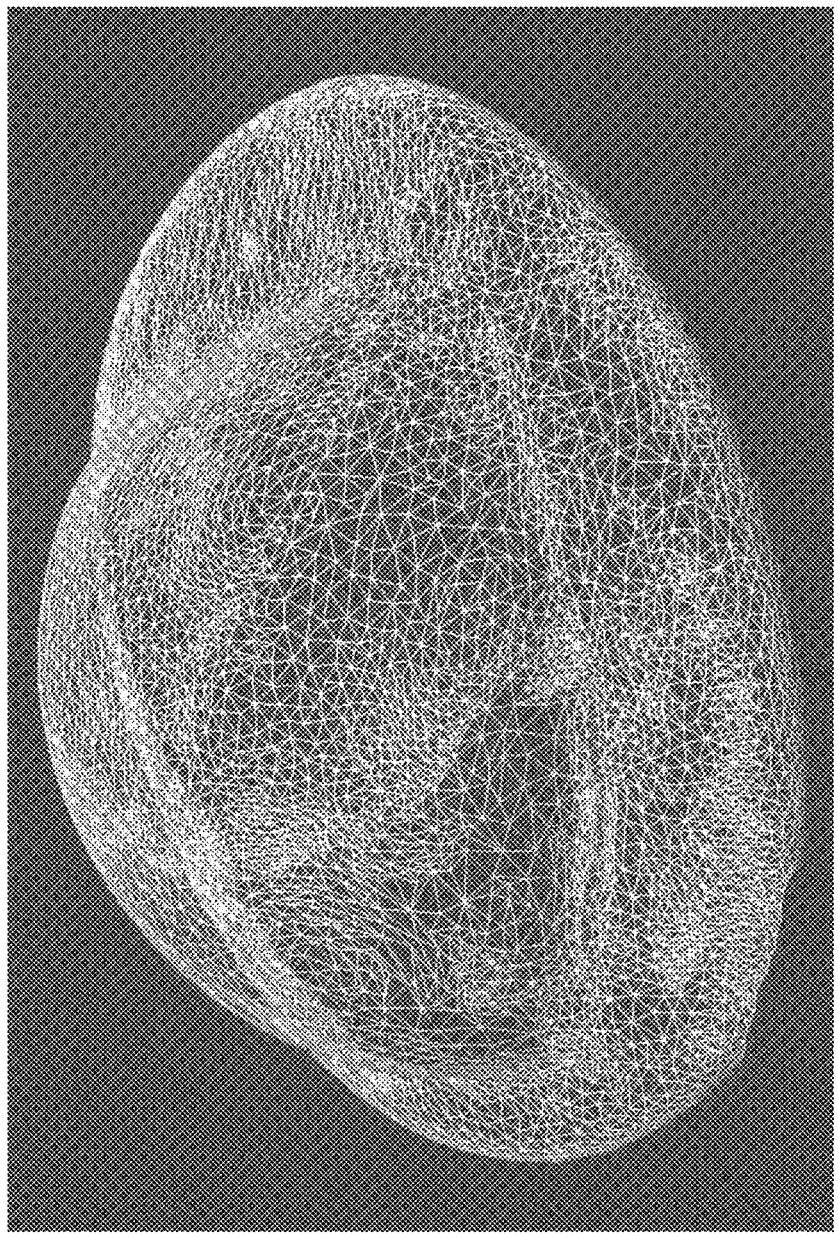
FIG. 7B depicts raw laser scan data of the articular surface.
Figure 7C:
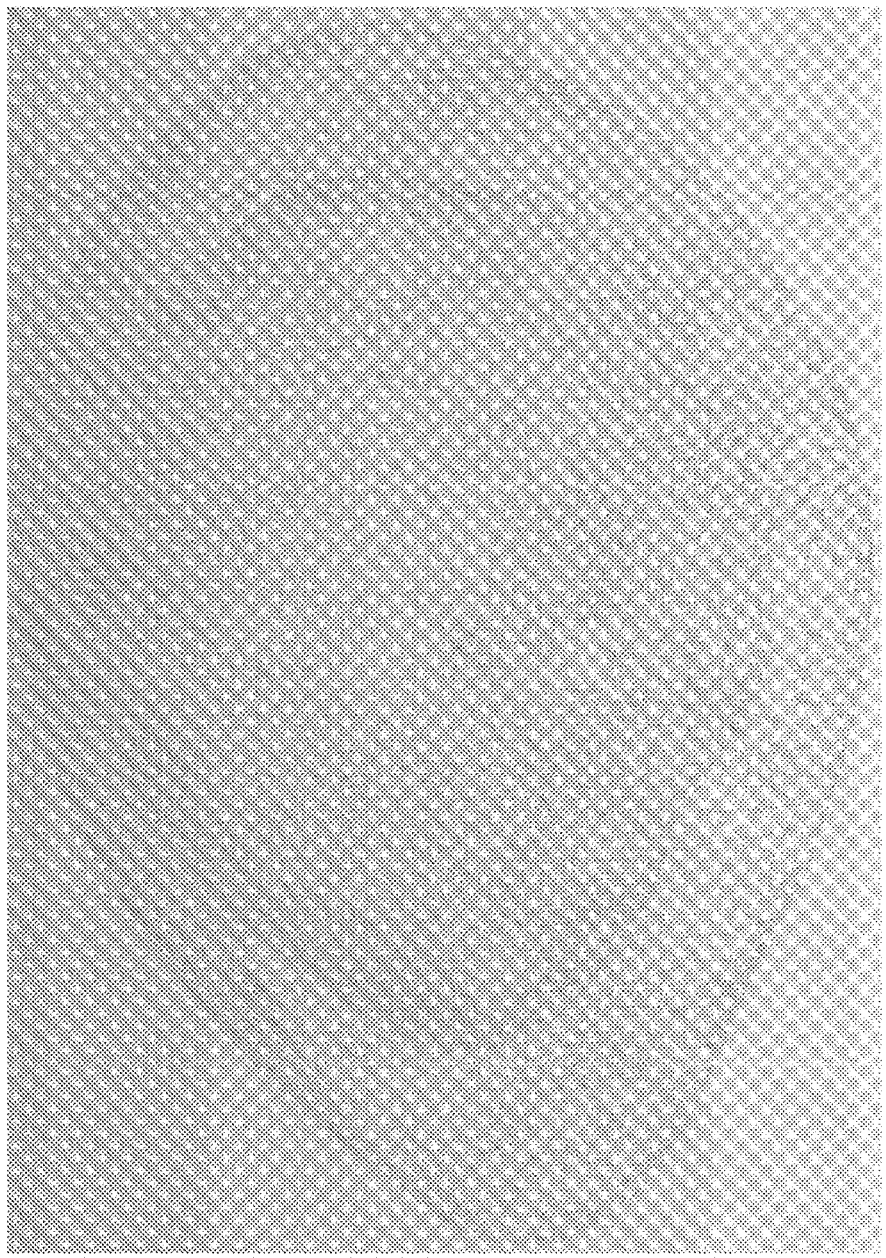
FIG. 7C depicts registered and trimmed articular surface and subchondral bone scan data.
Figure 7D:
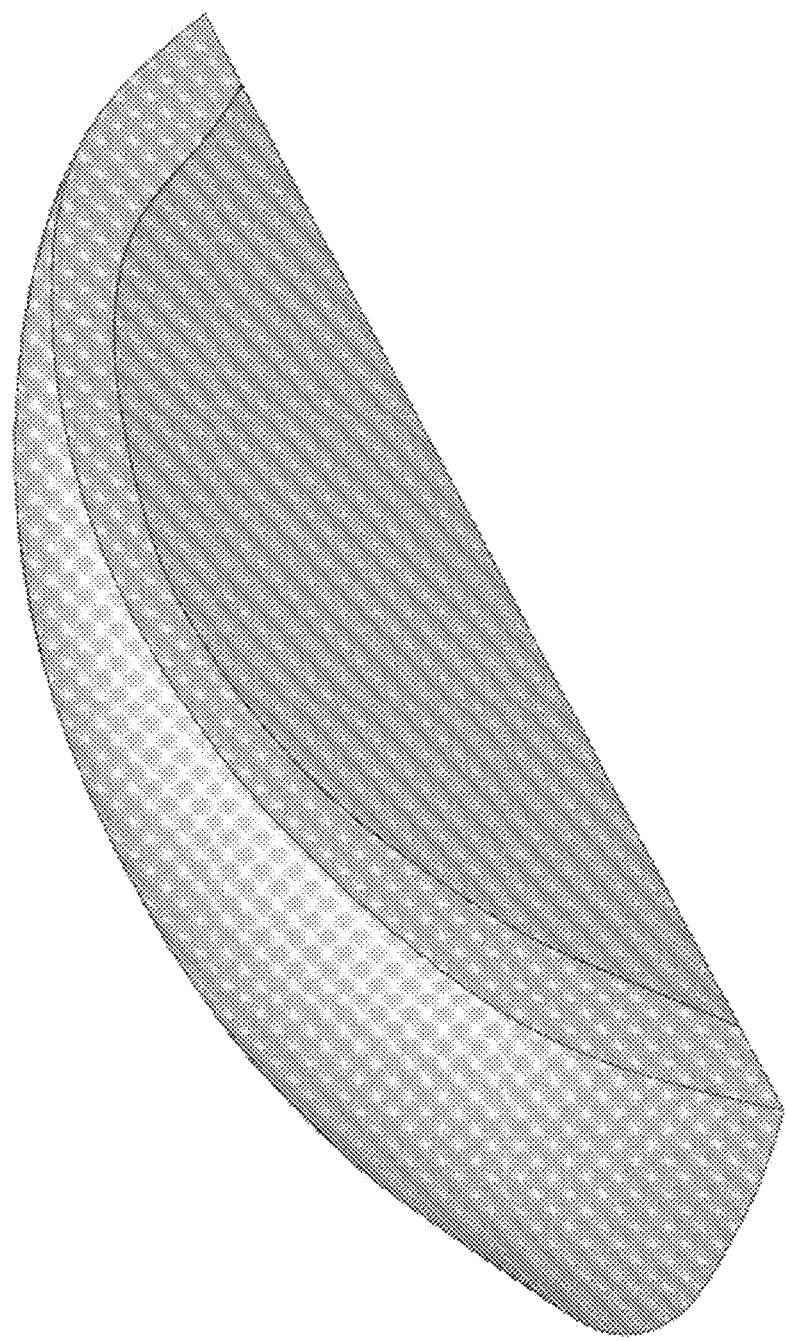
FIG. 7D depicts a B-spline model of articular layer, shown in cross-section.

The 3D points of the articular and subchondral bone surfaces are least-squares-fitted with a single biquintic spline or a piecewise-smooth bicubic Bspline (FIG. 7D). The best choice of spline type is based on a quantitative goodness of fit. These spline equations are used to characterize the principal curvatures of the articular surface and the thickness of the cartilage layer, all of which may be displayed using contour maps.

The maximum and minimum curvature maps (FIG. 4) are used to identify locations where these curvatures most closely match those of the trapezium articular surface (FIG. 3). Since the curvatures may vary continuously over the complex surface of a joint, the matching process relies on a regional averaging procedure that spans the typical surface area of the trapezium articular layer. The mean articular layer thickness at those locations is also characterized. The femoral, humeral, ulnar and talar trochleas are ranked in order of best-to-worst matches with regard to maximum and minimum curvatures, and cartilage thickness. Based on those results, two 'best' sources of osteochondral allografts are identified for the subsequent aims.

According to various embodiments of the present disclosure, all osteochondral allograft sources are identified that match the anatomy of the trapezium articular layer sufficiently closely while also exhibiting the desired cartilage thickness, as determined from their B-spline contours (FIGS. 8A and 8B). Based on the articular surface curvature measurements of these allografts, the amount of allograft bending required to reproduce the known curvature of the trapezium is determined. Using the measured geometry and existing databases of distal femoral articular layers, computer models are constructed of the osteochondral allografts with one or more cut grooves in the bony side of the model, whose width is adjusted to allow the necessary amount of bending (FIG. 8C), which illustrates a single tapered groove. The groove depth extends through the entire height of the bony side of the osteochondral allograft, so that bending only involves deformation of the cartilage layer. The height of the osteochondral allograft is set to about 7 mm, which is approximately half the height of the natural trapezium.

In some embodiments, these computer models of grooved allografts are meshed for the purpose of finite element modeling. In some embodiments, Cubit (https://cubit.sandia.gov/) is used for meshing. Since all the deformation from bending occurs in the cartilage, the bony blocks are modeled as rigid bodies, whereas the articular cartilage layer is modeled using a constitutive model of articular cartilage. In this model, the collagen matrix is described by a continuous fiber distribution where fibers may only sustain tension, and the proteoglycan ground matrix is modeled using Donnan equilibrium theory. This constitutive model of cartilage captures the tension-compression nonlinearity characteristic of this tissue. Representative material properties for the cartilage will be obtained from characterizations of human glenohumeral cartilage under finite strains, which includes property variations through the depth of the articular layer (inhomogeneity) as well as parallel and perpendicular to the split line direction (anisotropy).

Figure 9A:
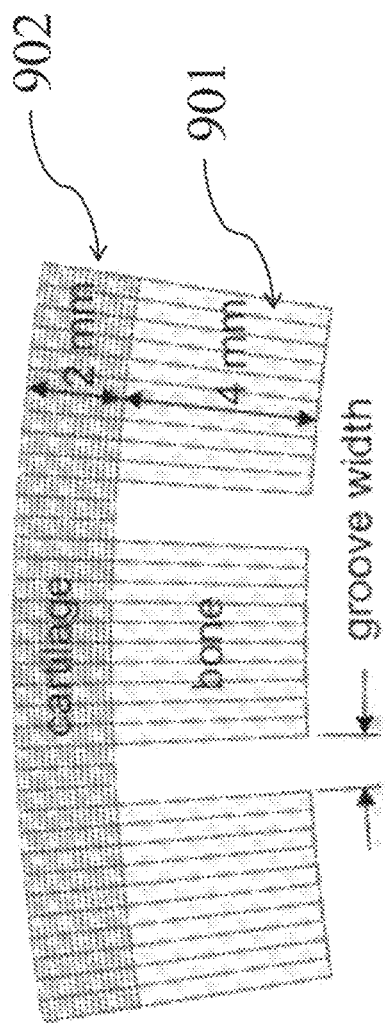
FIG. 9A is a side view of a finite element model of a grooved osteochondral allograft.
Figure 9B:
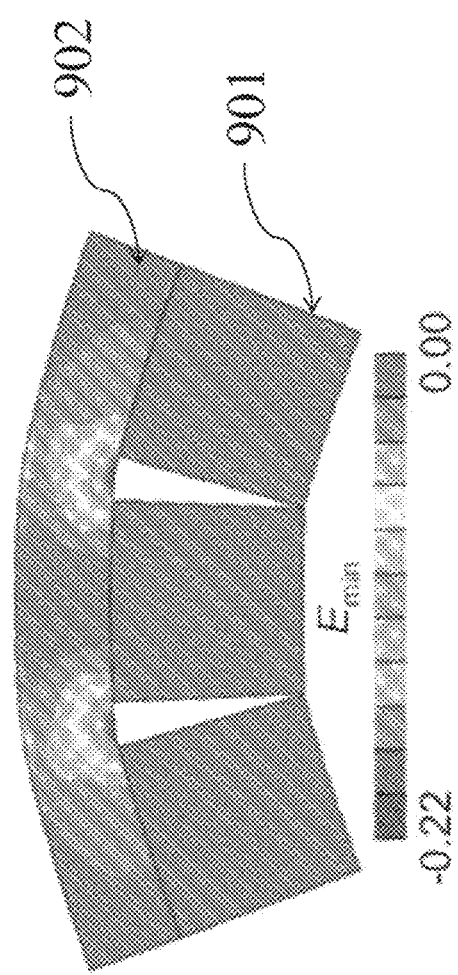
FIG. 9B depicts a bent allograft with contour map of minimum principal strain, $E_{min}$.
Figure 9C:
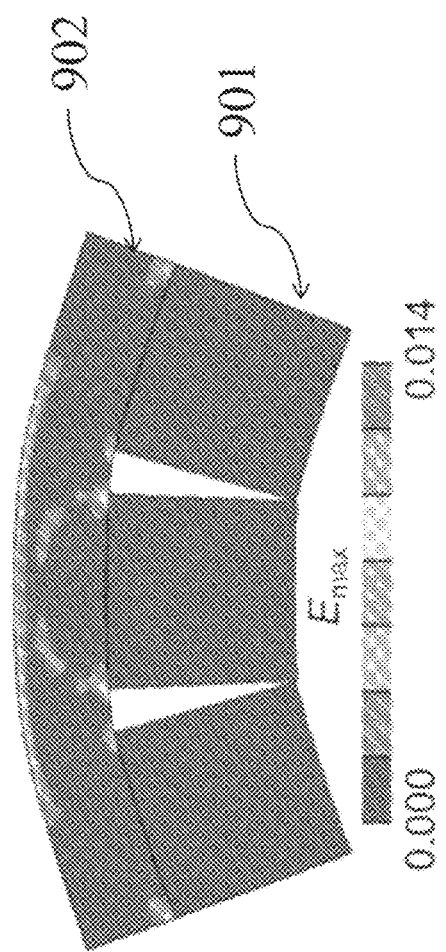
FIG. 9C depicts a map of maximum principal strain, $E_{max}$.

Referring to FIG. 9, in the finite element model, cuts in the bony portion of the allograft are designed to provide the desired bending of the allografts (FIG. 9A). Simulated bending is performed by prescribing rigid body motions to the underlying bony blocks 901, such that the final curvature of the articular surface 902 matches the corresponding curvature of the trapezium. Maps of the minimum (most compressive, FIG. 9B) and maximum (most tensile, FIG. 9C) principal strains are generated to determine whether they fall within the safe range (−50% to +16%).

Some osteochondral allografts only require bending along one direction (e.g., to increase the maximum curvature along the dorsal-volar direction, FIG. 1, or decrease the minimum curvature along the radial-ulnar direction) if one of their principal curvatures already falls within the range of trapezium articular surface curvature (as shown in the femoral trochlea, FIG. 4). Other allografts require bending along both directions, but by a lesser amount. Therefore, finite element simulations may investigate any of these combinations. The minimum number of grooves required for bending the allograft is one. In some embodiments, for practical purposes and because of the need to maintain sufficient bone stock, the maximum number of grooves is set to four regardless of the groove direction (dorsal-volar or radio-ulnar). If an allograft can be bent to the desired curvature with four or fewer grooves while maintaining a safe level of strain, this allograft source may be considered an acceptable choice.

In some embodiments, finite element parametric analyses provide guidelines on the number and width of grooves needed to reproduce the trapezium articular surface curvature from each proposed source of osteochondral allograft. Since the trapezium of females is smaller than that of males on average, the analyses of male and female joints are run separately, with the targeted curvatures based on gender. These gender-based guidelines may also serve as the basis for CMC allograft surgery guidelines.

In some embodiments, osteochondral allograft sources, along with their corresponding groove number and width, are selected from the finite element modeling step to exhibit safe cartilage strains under bending with the least number of grooves. Osteochondral allografts from these sources are harvested from fresh-frozen cadaver joints and grooves are created as prescribed above. The bent osteochondral allografts are transplanted in gender and size-matched cadaver hands, and in some embodiments, secured on the congruently shaped hemi-trapezial substrate using a biocompatible tissue adhesive (e.g., n-butyl-2-cyanoacrylate), fixation pegs, and/or headless or headed screws which are countersunk. Bent allografts are kept in that configuration using the tissue adhesive and, in some embodiments, a threaded K-wire or cerclage wire, if greater strength is required. Dorso-radial ligament reconstruction is performed. A control group of cadaver hands is treated similarly, except that the trapezium of that hand serves as its own source of osteochondral autograft. Thus, the distal half of the trapezium is excised and reimplanted in the same joint, using the same fixation, anchoring, and capsular reconstruction procedures.

To validate the strength of the allograft grooved and bent according to the methods described herein, the cadaver hand is potted within acrylic tubing using expansion cement and reinforced with K-wires, at the level of the scaphoid, and mounted on the bottom crosshead of a material testing system. The proximal and distal phalanxes of the thumb are resected and the metacarpal is similarly potted in acrylic tubing using dental cement extending from its distal end to its mid-diaphysis and reinforced with K-wires. The metacarpal end is connected to the top crosshead of the material testing system. The thumb joint is placed in a neutral position (zero flexion-extension, abduction-adduction and pronationsupination), and compressed along the length of the metacarpal under displacement control. The load is monitored during the compressive response. The test is terminated at failure, when a sudden decrease in load is observed.

This validation test provides a measure of the relative strength of grooved and bent osteochondral allografts in comparison to allografts that are neither grooved nor bent. Based on the biomechanics of the CMC joint, a healthy intact thumb joint should be able to sustain up to 1500 N of compressive load. If this objective is not met, or if the failure strength of bent allografts falls below 75% of that of autografts, the number and/or width of grooves and the amount of bending may be reduced until satisfactory strength measurements are achieved.

In some embodiments, live osteochondral allografts are procured. Control allografts are trimmed to the desired dimensions using a fine side-cutting burr. Grooved allografts undergo the same trimming as control samples and the desired number of grooves are created at the desired width. Bent allografts are processed as in the Grooved group and are additionally bent to achieve the desired curvature. Specimens in the Bent group are harvested from the allograft region matching the trapezial curvature most closely. All manipulations are performed under sterile conditions in a Class II biosafety cabinet. To validate the viability of cells in live osteochondral allografts that were grooved and bent according to the methods described herein, specimens from each group are cultured for four weeks. Allografts are cleaned of bone marrow with a high velocity water pick and cultured in a chemically defined serum-free and dexamethasone-free medium (DMEM, 1% ITS+Premix, 50 mg/ml L-proline, 0.9 mM sodium pyruvate) and supplemented with ascorbate 2-phosphate (50 mg/ml) (37° C., 5% $CO_2$). At the end of the culture period, the cartilage layer is assessed biochemically and mechanically, as well as for cell viability.

According to various embodiments of the present disclosure, the mechanical properties of the cartilage layer are evaluated non-destructively using a custom tabletop testing device modified to perform an indentation test with a spherical probe (θ3 mm), under stress relaxation to validate the method of producing allografts. The transient experimental response is fitted with the biphasic theory to extract the equilibrium compressive modulus ($E_{-y}$), the equilibrium tensile modulus ($E_{+y}$, and the hydraulic permeability (k).

In some embodiments, after mechanical testing, for validation purposes, the cartilage excised from one half of each allograft is weighed wet, lyophilized, reweighed dry, and digested in 0.5 mg/ml Proteinase-K (in 50 mM Tris buffered saline containing 1 mM EDTA, 1 mM iodoacetamide and 10 mg/ml pepstatin A) at 56° C. for 16 h. The PicoGreen assay is used to quantify the DNA content of the explant disks with Lambda phage DNA (0-1 mg/ml) as a standard. The GAG content is measured using dimethylmethylene blue (DMMB, Sigma Chemicals) dye-binding assay with shark chondroitin sulfate (0-50 mg/ml) as a standard. Collagen content is assessed by measuring orthohydroxyproline (OHP) content via dimethylaminobenzaldehyde and chloramine T assay. Collagen content is calculated by assuming a 1:7.5 OHP-to-collagen mass ratio. The collagen and GAG contents are normalized to the disk wet weight and DNA content.

Fluorescent viability stains, such as the one reported in FIG. 6, may overestimate chondrocyte viability in long-term cultures of osteochondral allografts. To overcome this limitation, in some embodiments, an alternative approach based on cell counting is employed. Cartilage from the second half of each osteochondral allograft is harvested and digested with the same protocol used for harvesting chondrocytes in tissue engineering studies. Cartilage is diced into approximately 1 $mm^3$ chunks, rinsed in DMEM supplemented with 10% FBS, amino acids, buffering agents, and antibiotics. The cartilage chunks are digested with 50 mg of bovine testicular hyaluronidase type I-S(Sigma) in 100 ml of DMEM for 30 minutes at 37° C. After removal of the hyaluronidase solution, the cartilage specimens are digested at 37° C. overnight with 50 mg of clostridial collagenase type II (Sigma) in 100 ml of DMEM. The cell suspension is then sedimented in a benchtop clinical centrifuge at 4° C. for 5 minutes. After rinsing the pellets by resuspension in 20 ml of DMEM and centrifugation, the cells are resuspended in 10 ml of DMEM. Only intact (live) cells remain in this solution. Cells per mL of tissue are counted using a Coulter Counter (Multisizer 4, Beckman Coulter, Brea, Calif.), to provide a quantitative measure for statistical analyses.

In some embodiments, ANOVAs with repeated measures are used for validation purposes, to compare the mechanical properties ($E_{-y}$, $E_{+y}$, k), GAG and OHP per wet weight, and live cell density, among the three groups. Statistical comparisons inform whether grooving alone, or grooving and bending, significantly compromise live allograft viability or mechanical and compositional integrity.

According to various embodiments of the present disclosure, a computer readable storage medium is provided having computer readable program instructions thereon for causing a processor to carry out aspects of the present invention. The computer readable storage medium may be, for example, an electronic storage device, a magnetic storage device, an optical storage device, an electromagnetic storage device, a semiconductor storage device, or any suitable combination thereof. In various embodiments, the computer readable program instructions may be located on the same computing node as the processor executing them. In other embodiments, the program instructions are retrieved via a network, bus, or other digital transport prior to execution. In yet other embodiments, the program instructions are divided between the computing node having the processor and a remote location. The processor may be included in a general purpose or special purpose computer.

According to various embodiments of the present disclosure, a customized osteochondral graft is provided as a part of a surgical kit for implanting that graft. In some embodiments, the surgical kit includes spacer jigs corresponding to graft thickness to assist the surgeon in regaining a stable joint. The use of the spacer jig allows the surgeon to prepare the diseased joint to exactly fit the allograft by acting as a guide for making incisions in the diseased joint.

According to various embodiments of the present disclosure, automated methods are provided for cutting grooves in osteochondral allografts. In some embodiments, a milling machine, such as a benchtop computer numerical control (CNC) milling machine employing straight or tapered end mills, is used for shaping the allograft. In such embodiments, the mills are passed over the surface of the allograft to remove material, leaving grooves to allow the allograft to bend. Alternatively, slitting saw blades may be used for cutting the grooves. These are mounted on the CNC milling machine. Slitting saw blades may have a uniform thickness to cut grooves with uniform width. A CNC milling machine may be outfitted with a tool changer that holds slitting saw blades with different widths, so that each tool may be used in sequential passes to create a step-taper groove geometry. Customized slitting saw blades also may be used, which have a tapered cross-section, or staggered thicknesses, to cut grooves whose width varies with the depth of cut. Grooves may be cut manually by a skilled operator using a bandsaw. This approach has been shown to be effective and may be preferred in some manufacturing settings, such as tissue banks, where skilled workers are accustomed to performing accurate manual operations. In different embodiments, various speeds and mills or saws are used to achieve corresponding groove depths and widths. In some embodiments, a computer numerical control milling machine is small enough to fit in a biological hood to maintain sterility. A laser scan of the osteochondral allograft is used to estimate the correct depth of the groove to be cut in the allograft. Groove depth affects the allograft's flexibility and strength, as discussed further above, and the laser scan allows for higher accuracy cuts. A fiber optic light transmission and deflection through the groove is used to refine the depth of the cut. In any of these embodiments, the width and number of the groove(s) to be cut in the bone portion of the graft is determined as discussed herein.

In some embodiments, computer-controlled grips, clamps, vises and similar devices, including robots, are used to hold the allograft relative to the tools cutting the grooves.

Referring to FIG. 10, an automated method for cutting grooves is provided. Grooves are cut automatically while the osteochondral allograft is held and manipulated by a two-axis motorized clamp during cutting and finishing. In FIG. 10A, allograft 1003 is gripped along a first axis by clamp 1001. In FIG. 10B, grooves 1005 are cut perpendicular to the axis being held by clamp 1001. As shown in FIG. 10C, allograft 1003 is then clamped along a second axis by clamp 1002, parallel to the grooves, and clamps 1001 on the first axis are released. The allograft is held along the second axis for finishing.

The two-axis motorized clamp 1000, discussed above, comprises two sets of adjustable parallel plates, 1001 and 1002, controlled by motorized clamp screws 1004 that adjust the distance between the parallel plates. The two sets of parallel plates move independently and can both be tightened onto the allograft or released at the same or different times.

In some embodiments, upon completion of all cutting operations, the allograft may be held in a holding device that maintains the prescribed joint shape and contours until the allograft is delivered to operating room for transplantation. In some embodiments, the holding device also serves as an insertion tool for the positioning of the graft after the osteotomy cuts have been made.

In some embodiments, allografts are transplanted using fixation pegs, and/or headless, or headed screws which are countersunk. Using headless or countersunk headed screws avoids profile-related issues at the insertion site. The fixation materials may be titanium, stainless steel, PEEK, or PLA, PGA, or similarly approved materials for surgical fixation devices.

Exemplary Surgical Procedure

In an exemplary surgical procedure according to embodiments of the present disclosure, a distal femoral trochlea is used as an osteochondral allograft source. Groove number and width are computed to minimize mechanical damage to the articular layer. In particular, stress and strain concentrations are modeled and minimized as described above. If necessary, the projected bone deformation is also modeled.

Figure 11G:
Figure 11I:
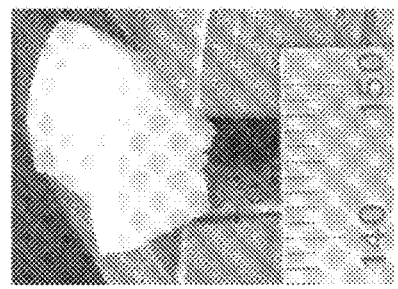
Figure 11H:
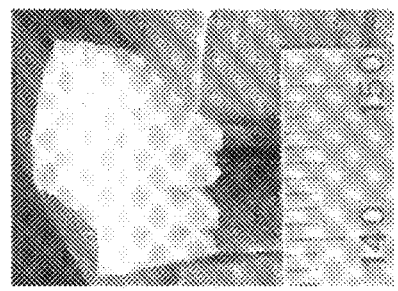

Referring to FIG. 11, a bent cadaver femoral trochlea is transplanted as an osteochondral allograft source into a cadaver hand, and then tested for mechanical strength. As shown in FIG. 11A, a diseased thumb trapezium bone is hemi-sected. Next, the knee allograft is resected as shown in FIG. 11B. The trapezium surface 1101 is shown next to the uncut osteochondral allograft 1102 in FIG. 11C. The distal femoral trochlea 1102 is measured and bent to the correct curvature, as seen in FIGS. 11G-11I. The bent osteochondral allograft 1103 is transplanted beneath the metacarpal bone 1101 as shown in FIG. 11D. Next, the joint capsule is reconstructed, as shown in FIG. 11E. The thumb is shown in FIG. 11F to have recovered its range of motion.

Additional embodiments of the methods for preparing a customized osteochondral allograft are described in the following. They demonstrate the feasibility of safely and reproducibly cutting grooves to bend human tissue femoral allografts to curvatures suitable for trapezium arthroplasty.

Figure 12:
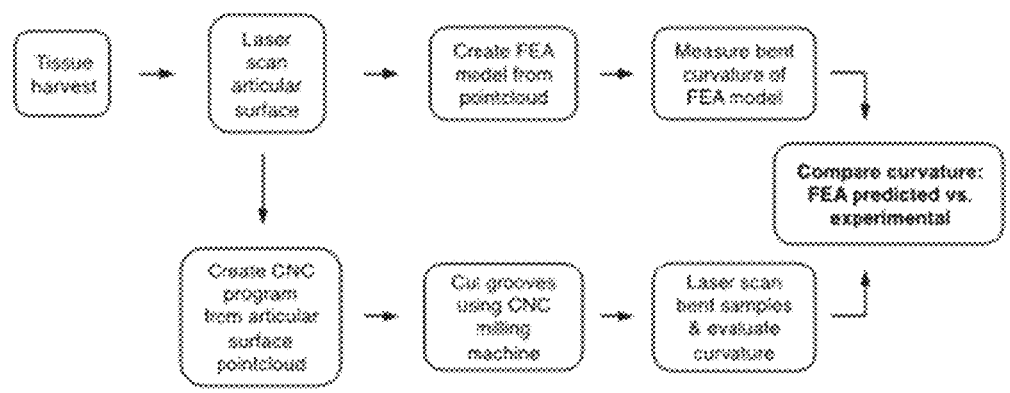
FIG. 12 shows a flowchart for validating curvature design and production.

FIG. 12 shows a flow chart for validating the methodology for designing and cutting grooves in the allografts. The surfaces of harvested grafts are scanned and used to create a finite element analysis model from the pointcloud data from the scan and a projected curvature of the bent graft is obtained. The pointcloud is also used to generate a cutting plan for the computer numerical control (CNC) machine to cut grooves in the allograft. After the grooves are cut, the bent allograft is rescanned by the laser and the actual experimental curvature results can be compared to the results predicted from the FEA. The comparisons can be used iteratively to refine the model so that one can reliably use the techniques to prepare allografts with desired curvatures for implant to a host.

Prior data sets were used to identify population average curvatures of the trapezium and femoral trochlea. These studies used stereophotogrammetry or magnetic resonance imaging to characterize the articular cartilage topography of human cadaver samples. Results showed that the concavity (minimum curvature) at these locations matched within the standard deviation and would not require bending, but the convexity (maximum curvature) differed more significantly: the average for the femur was $\kappa=40\pm12$ m$^{-1}$ compared to $\kappa=146\pm46$ m$^{-1}$ for the trapezium, as shown in Table 1. These results were used herein as the acceptable target curvature range for bent osteochondral allografts. Grooves are desirably designed so that upon bending, the convex curvature of femoral allograft samples increases to this target range of $\kappa=146\pm46$ m$^{-1}$.

TABLE 1

Curvature of Femur and Trapezium

| Curvature | Trapezium (center) | Femur (middle) |
|---|---|---|
| maximum [m$^{-1}$] | 146 ± 46 | 40 ± 12 |
| minimum [m$^{-1}$] | −95 ± 26 | −103 ± 33 |

Figure 13:
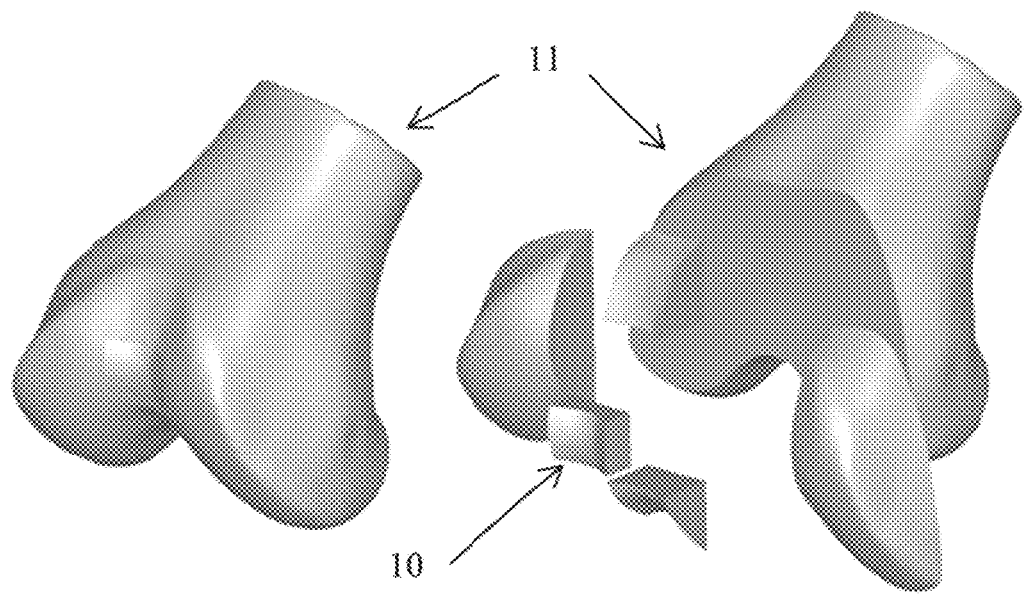
FIG. 13 shows drawings of a dissection plan for cutting rough stock samples of allografts from human femurs using a bandsaw.
Figure 14:
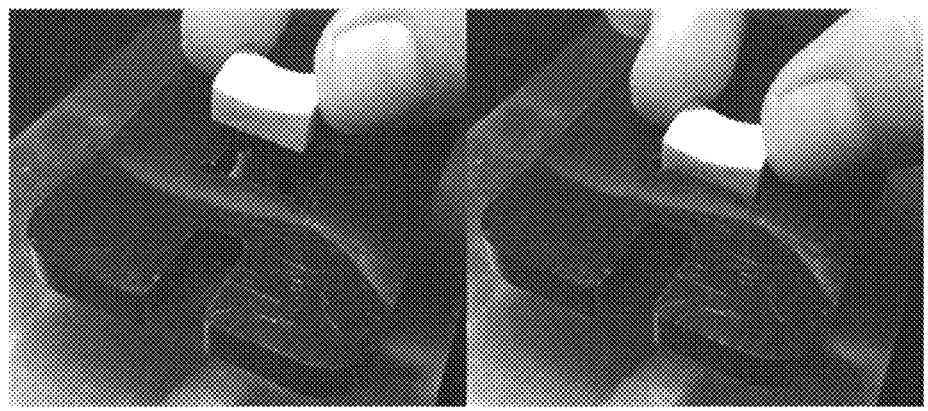
FIG. 14 shows photographic images of using an inspection gauge to measure dimensions of a harvested allograft.

Sample dissections were used to demonstrate dissecting allografts from the cadaver femurs. Five human knee joints were obtained from a tissue bank (2 female, 3 male, ages 57-73, median age 60) and sharp-dissected free of muscle and soft tissue. Using a miniature bandsaw (Micro-Mark, Berkeley Heights, N.J.), femurs 11 were cut as shown in FIG. 13 to provide trapezium allograft rough stock samples 10 with shape and size (16 mm×12 mm×10 mm) determined from published average measurements of trapezium bone CT scans. During cutting, a custom-designed inspection gauge (FIG. 14) was used to iteratively verify the dimensions of each rough stock sample. This tool was designed to allow repeatable, precise sample measurement with easier cleanup and disinfection compared to standard measurement calipers.

Figure 15:
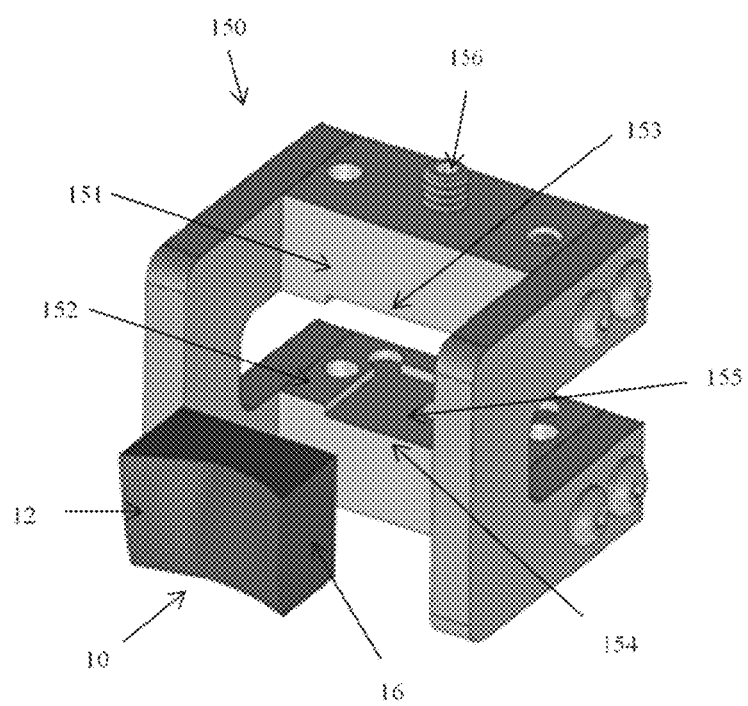
FIG. 15 is a drawing of a clamping device for holding the allograft during scanning and cutting procedures.

Once cut to size, each rough stock allograft sample 10 (obtained from a femur dissection as shown in FIG. 13) was clamped in a custom-designed fixture 150, shown in FIG. 15. Since the CNC tool paths for groove cutting were programmed based on articular surface laser scan point clouds, the clamping fixture was designed to accommodate both scanning and machining operations yet firmly clamp the sample. The clamping fixture comprises two spaced-apart parallel plates 151 and 152 in fixed configuration with recesses 153 and 154 adapted to define a seat 155 for receiving the allograft 10. Seat 155 provides access for scanning the surface of the cartilage layer 12 of the allograft 10 and access to the bone portion 16 of the allograft 10 for machining of grooves. Screw 156 is used to secure the alloagraft 10 in the seat 155. Fixtures 150 were bolted to magnetic optical bases 182, not shown, (SB-1, Thorlabs, Newton, N.J.) to facilitate repeatable positioning in the laser scanner and CNC coordinate systems. Five sample holders were manufactured so that each sample remained firmly clamped between the scanning and machining step.

The cartilage articular surface of each sample was scanned with a 3D laser scanner (NextEngine, Santa Monica, Calif.). Each scan took approximately 20 seconds and yielded 3D point cloud data with about 0.5 mm spacing and about 0.125 μm accuracy. After scanning, samples in their fixtures were kept submerged in phosphate-buffered saline, protease inhibitor and biocide at 4° C. until machining took place.

Point cloud data from each sample articular surface scan was imported into the computer-aided design software Solidworks (Dassault Systémes, version 2014, Vélizy-Villacoublay, France) and fitted with a single B-spline surface. To create the cartilage volume, this B-spline surface was copied and offset by the average caliper measurement of the cartilage layer thickness on the four sides of the sample. The bone volume was created using sample measurement dimensions. Groove geometries were chosen based on off-the-shelf standard tool dimensions.

Solid model geometries were meshed using the Cubit meshing software (cubit.sandia.gov, version 13.2). Articular cartilage 12 layers were meshed using 8-node hexahedral elements with a biased, 5-element scheme through the thickness (FIG. 16). Bone portions 16 were modeled as rigid, undeformable bodies and thus were surface meshed relatively coarsely using hex face elements. Meshes were imported into FEBio (febio.org) to prescribe cartilage material properties and boundary conditions.

The articular layer 12 was modeled as an elastic material with a solid matrix consisting of a mixture of a neo-Hookean elastic solid (Young's modulus E and Poisson's ratio ν, FEBio User Manual 2.3, section 4.1.3.15), representing the proteoglycan ground matrix, and a continuous fiber distribution (fiber modulus ξ and power-law exponent β, sections 4.2.1, 4.2.3.1, and 4.2.4.1), representing the collagen. The models are shown in unbent (FIG. 16A) and bent configurations (FIG. 16B). To simulate bending deformation, one node on either side of each groove 18 was displaced along a line connecting the two points. Full bending was achieved in a steady-state analysis, typically in ten 0.1 s steps over 1 s total. Maximum curvature k of the articular surface of each model at each solution time step was evaluated using the custom algorithm described below.

Point cloud data from each articular surface laser scan was also used to generate CNC tool paths for groove cutting. Using a custom algorithm, point cloud data was first fitted with a single quadratic B-spline surface (order=3, coefficients=3). Next, this algorithm calculated the curve formed by the intersection of the fitted surface with three parallel planes separated by a user-defined distance corresponding to the desired groove spacing. The resulting three curves were then offset in a direction normal to the B-spline surface by a user-defined distance, calculated by summing the tool blade radius, the measured cartilage thickness, and if needed, any additional offset, e.g. multiple paths of increasing offset were used to create a step-taper groove geometry. Offset curves were discretized into 20 points each and exported as a single, unsorted point cloud data file. Next, a custom MATLAB algorithm sorted the offset curve point cloud data into a structured toolpath. This toolpath (FIG. 17) was converted to machine-readable CNC G-code commands, combined with cutting speed and feed parameters and starting and stopping commands, and finally saved as a text file. In the tool path shown in FIG. 17, three cuts were programmed to be made in the graft, with the length of cut plotted on the x-axis, the depth of cut plotted on the y-axis, and the spacing of the grooves plotted on the z-axis.

Grooves with a step-taper geometry were cut in each sample by using three slitting-saw blades (Malco, Cranston, R.I.) with gradually decreasing kerf size and increasing path offset. Because the smallest final cut (0.02-inch blade) did not completely remove bone at the base of the groove, all samples required hand finishing to achieve flexibility. This was done by gently passing each sample over a thin 0.02-inch blade clamped vertically in a vise until the sample was flexible. Grooved samples were bent and rescanned, then these point clouds were evaluated for articular surface maximum curvature using the algorithm described above.

Accurate CNC machining using point cloud data from the laser scanner required a method of transforming between the local coordinate systems of the two machines. In general, six degrees of freedom were required for the complete transformation for each of the five sample holders. In practice, because the scanner coordinate system was aligned with the real world horizontal and vertical axes, only two rotations were needed and were reused for each sample holder. Unique translations were used for each and were calculated using two custom-designed reference blocks 180 (FIG. 18A) and shown in the clamping device 150 of FIG. 15 (FIG. 18B), also attached to magnetic kinematic bases 182 (SB-1, Thorlabs, Newton, N.J.) shown in FIG. 18C. Spherical surfaces 181 on each of the two blocks were scanned to obtain point clouds, then these data were least-squares fitted with the analytical sphere equation to obtain the sphere center. This calculated sphere center combined with the known outer dimensions of each reference block were sufficient to touch-reference the CNC and reconcile the two coordinate systems.

FIGS. 19A and 19B shows photographic images of a human osteochondral allograft from a knee femoral groove, grooved with CNC-controlled slit saws using a staggered pattern of decreasing groove width, shown in the FIG. 19A in unbent configuration and a back view of the same allograft, clamped in a bent configuration is shown in FIG. 19B. The images illustrate the increase of curvature in the graft in the direction perpendicular to the orientation 13 of the grooves 18, and negligible change in the curvature in direction parallel 15 to the grooves 18. These images can be compared to the FEA designed grafts in FIGS. 16A and 16B, which show similar changes in curvature.

While the disclosed subject matter is described herein in terms of certain exemplary embodiments, those skilled in the art will recognize that various modifications and improvements may be made to the disclosed subject matter without departing from the scope thereof. Moreover, although individual features of one embodiment of the disclosed subject matter may be discussed herein or shown in the drawings of the one embodiment and not in other embodiments, it should be apparent that individual features of one embodiment may be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. A customized osteochondral graft comprising:
an uninterrupted cartilaginous layer having a first surface disposed on a bone portion, the bone portion having one or more grooves cut across the width of the bone portion; wherein each groove depth extends through the height of the bone portion, the customized graft is bendable into a shape that conforms to a host site, and wherein bending is localized in the cartilage layer.

2. The customized osteochondral graft of claim 1, wherein the uninterrupted cartilaginous layer is convex along one direction and concave along the corresponding perpendicular direction.

3. The customized osteochondral graft of claim 1, wherein the uninterrupted cartilaginous layer has a thickness of about 2 mm.

4. The customized osteochondral graft of claim 1, wherein the bone portion has a thickness of about 4 mm.

5. The customized osteochondral graft of claim 1, wherein the bone portion comprises a plurality of bone portions separated by a plurality of grooves.

* * * * *